United States Patent
Fujimura et al.

(10) Patent No.: US 7,186,784 B2
(45) Date of Patent: Mar. 6, 2007

(54) PHOSPHORUS-CONTAINING CARBOXYLIC ACID DERIVATIVES PROCESS FOR PREPARATIONS THEREOF AND FLAME RETARDANT

(75) Inventors: Toshinobu Fujimura, Aichi (JP); Kazunori Waki, Aichi (JP); Koji Sato, Aichi (JP); Shiro Mibae, Aichi (JP)

(73) Assignee: NOF Corporation, Tokyo (JP)

(*) Notice: Subject to any disclaimer, the term of this patent is extended or adjusted under 35 U.S.C. 154(b) by 326 days.

(21) Appl. No.: 10/488,858

(22) PCT Filed: Sep. 20, 2002

(86) PCT No.: PCT/JP02/09675

§ 371 (c)(1),
(2), (4) Date: Mar. 8, 2004

(87) PCT Pub. No.: WO03/027208

PCT Pub. Date: Apr. 3, 2003

(65) Prior Publication Data

US 2004/0249028 A1    Dec. 9, 2004

(30) Foreign Application Priority Data

Sep. 20, 2001 (JP) ............... 2001-287580
Dec. 14, 2001 (JP) ............... 2001-382317
May 8, 2002 (JP) ............... 2002-132302

(51) Int. Cl.
*C07F 9/32* (2006.01)
*C07F 9/40* (2006.01)
*C08K 5/5313* (2006.01)
*C08K 5/5317* (2006.01)
*C08L 63/02* (2006.01)

(52) U.S. Cl. ............... 525/508; 525/326.5; 525/327.3; 525/328.2; 525/328.5; 525/328.8; 525/329.9; 525/340; 525/408; 525/451; 525/454; 525/471; 525/472; 525/514; 525/533; 556/19; 556/20

(58) Field of Classification Search ............... 558/82, 558/179, 180
See application file for complete search history.

(56) References Cited

U.S. PATENT DOCUMENTS

| | | | | |
|---|---|---|---|---|
| 4,127,590 A | 11/1978 | Endo et al. | ............... | 528/287 |
| 5,444,123 A | 8/1995 | Zeltner et al. | ............... | 525/133 |
| 5,773,533 A | 6/1998 | Hörold | ............... | 525/533 |
| 5,847,184 A | 12/1998 | Kleiner | ............... | 558/73 |

FOREIGN PATENT DOCUMENTS

EP    1059323    12/1999
JP    07082351    3/1995

OTHER PUBLICATIONS

CAPLUS accession No. 1995:951018 for the Russion Journal of General Chemistry, Gazizov et al., 1995, 2 pages, abstract.*
CAPLUS accession No. 1993:651315 for European Patent No. 530,692, Zeltner et al., Mar. 10, 1993, 3 pages, abstract.*
CAPLUS accession No. 1998:621121 for PCT Publication No. WO 98/40078, Rephaeli, Sep. 17, 1998, 6 pages, abstract.*
CAPLUS accession No. 2001:472731 for PCT Publication No. WO 2001/046206, Leblanc et al., Jun. 28, 2001, 4 pages, abstract.*
А.И. Разчмоб et al., ВЗАИМОДЕЙСТВИЕ ФОСФОРИЛИРОВАННЫХ АЛКИЛВИНИЛОВЫХ ЭФИРОВ С КАРБОНОВЫМИ КИСЛОТАМИ И СПИРТАМИ, Zh. Obshch.Khim., 1974, vol. 44, No. 2, pp. 458 to 459, particularly, p. 458, last line to p. 459, line 1, $RR'P(O)CH_2$ $CH_2OCH(CH_3)OC(O)CF_3$.
М.В. Газизов et al., ВЗАИМОДЕЙСТВИЕ АЛЬДЕГИДОВ, АКТИВИРОВАННЫХ ТРИАЛ КИЛФОСФИТАМИ, С АНТИДРИДАМИ КАРБОНОВЫХ КИСЛОТ, Zh. Obshch.Khim., 1974, vol. 65, No. 7, p. 1226, particularly, p. 1226, compound V, $(R^1O)_2P(O)CH(R^2)OCH(R^2)OCOR^3$.
A.I. Razumov, et al., "Reactions of Phosphorylated Alkyl Vinyl Ethers With Carboxylic Acids and Alcohols", *Journal of General Chemistry USSR*, vol. 44, No. 2, Feb. 1974, p. 438.
M.B. Gazizov, et al., "Reaction of Aldehydes Activated by Trialkyl Phosphites With Carboxylic Acid Anhydrides", *Russian Journal of General Chemistry*, vol. 65, No. 7, part 2, Jul. 1995, p. 1116.

* cited by examiner

Primary Examiner—Robert Sellers
(74) Attorney, Agent, or Firm—Antonelli, Terry, Stout and Kraus, LLP.

(57) ABSTRACT

There are disclosed a phosphorus-containing carboxylic acid derivative which has a group containing phosphorus atom and has in its molecule, a group represented by the following formula (1):

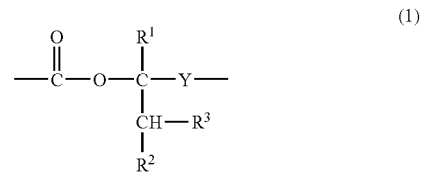

(1)

wherein $R^1$, $R^2$ and $R^3$ are each hydrogen atom or a hydrocarbon group having 1 to 18 carbon atoms, and Y is oxygen atom or sulfur atom; a process for producing the derivative; and a flame retardant comprising the foregoing derivative as an effective ingredient. The present invention can provide the phosphorus-containing carboxylic acid derivative and a flame retardant which are each excellent in solubility in an organic solvent, compatibility with a variety of resins, stability and flame retardancy.

35 Claims, 10 Drawing Sheets

PHOSPHORUS-CONTAINING CARBOXYLIC ACID DERIVATIVES PROCESS FOR PREPARATIONS THEREOF AND FLAME RETARDANT

TECHNICAL FIELD

The present invention relates to a phosphorus-containing carboxylic acid derivative which is utilized as a resin molded article, flame retardant, coloring preventive agent, heat resistance-imparting agent, curing agent for a thermosetting resin and the like; a process for producing the above-mentioned derivative; and usage thereof. More particularly, the present invention concerns with a phosphorus-containing carboxylic acid derivative which is excellent in solubility in an organic solvent, compatibility with a variety of resin and storage stability in blending with a resin, and which can impart a favorable and suitable resin composition to a resin molded article, covering material, adhesive and the like each requiring flame retardancy; a process for producing the above-mentioned derivative; and usage such as a flame retardant.

BACKGROUND ART

In general, a synthetic resin molded article which requires flame retardancy is blended with any of various flame retardants such as a phosphorus based flame retardant and a halogen based flame retardant. These flame retardants are required to be resistant to the heat, acting in the case of molding and processing a synthetic resin or using a product after molding and at the same time, are desired not to impair the performances inherent in the synthetic resin such as water resistivity and physical performances.

However, the phosphorus-containing compounds which have hitherto been used as a flame retardant suffer from such defects that impair physical characteristics of a synthetic resin, deteriorate the stability and water resistivity and so forth, since most of the compounds have been each an additive-type flame retardant. In addition, since most of the phosphorus-containing compounds that are used each as an additive-type flame retardant are poor in compatibility with a resin, there have been brought about the problem that the compounds are difficult to homogeneously blend in the resin, even if homogeneous blending is possible, the problem that the flame retardant bleeds out from the molded article after molding, thus failing to maintain the working effect thereof and also the problem on external appearance.

In order to overcome the above-mentioned problems, a phosphorus-containing epoxy resin is proposed {refer to Japanese Patent Application Laid-Open No. 279258/1999 (Hei 11)}. The aforesaid epoxy resin, in which phosphorus-containing groups are chemically bonded to the resin matrix after molding, can become a flame retardant excellent in water resistivity and stability, while maintaining resin characteristics to some extent. Nevertheless, the phosphorus-containing epoxy resin is inferior in solubility in much of organic solvents and in compatibility with a variety of resins, thereby limiting the blending formulations thereof. It also involves the problem that it is inapplicable alone to the purpose of the use which requires high flame retardancy because of a low concentration (2.5% by weight or lower) of phosphorus atoms that can be blended in a resin and the like.

On the other hand, although some consideration is given to a phosphorus-containing carboxylic acid having phosphorus atoms and further a carboxylic group which reacts with an epoxy group as an excellent reactive flame retardant, the carboxylic acid involves the problem about general purpose properties because of its being inferior in solubility in much of organic solvents and in compatibility with a variety of resins as mentioned hereinbefore. In addition, since the carboxylic group and a reactive group are prone to react with each other, the carboxylic acid further creates the problem about the stability in that a composition in which the phosphorus-containing carboxylic acid and a compound containing the aforesaid reactive group coexist causes gelation during storage, limits a usable hour from blending to application and so forth.

Moreover a process for producing the above-mentioned phosphorus-containing carboxylic acid involves several problems as described hereunder. The phosphorus-containing carboxylic acid, especially a phosphorus-containing dicarboxylic acid has been produced, for instance, by allowing a phosphorus compound bearing a P—H bond such as 9,10-dihydro-9-oxa-10-phosphaphenanthrene-10-oxide to react with an unsaturated dicarboxylic acid such as fumaric acid, maleic acid or itaconic acid. The reaction is that called Michael addition reaction between the P—H bond in the phosphorus compound and C=C double bond in the unsaturated dicarboxylic acid. The reaction has been put into practice by mixing the phosphorus compound with the unsaturated dicarboxylic acid and heating the resultant mixture to a temperature in the range of 160 to 200° C., but has suffered the disadvantages of difficult temperature control due to the reaction being exothermic and also difficult separation of the phosphorus-containing dicarboxylic acid obtained after the reaction from the starting raw materials containing the phosphorus compound and the unsaturated dicarboxylic acid. Hence, in spite of being an extremely useful substance, the phosphorus-containing dicarboxylic acid is poor in productivity, is expensive in production cost and contains a large amount of the starting raw materials as impurities, whereby the practical application thereof is generally difficult.

In order to overcome the above-mentioned problems, there is disclosed a process for synthesizing the phosphorus-containing dicarboxylic acid at a reaction temperature in the range of 100 to 200° C. by the use of a lower saturated aliphatic monocarboxylic acid having 1 to 5 carbon atoms as a solvent {refer to Japanese Patent Application Laid-Open No. 176171/1996 (Hei 8)}. According to the above-mentioned production process, it is made possible to obtain a highly pure phosphorus-containing carboxylic acid in high yield by relatively removing generated heat upon the reaction of the phosphorus-containing carboxylic acid at a comparatively low temperature. However, the aforesaid lower saturated aliphatic monocarboxylic acid, which is a highly corrosive solvent having strong irritating-smell, is problematic in that perfect removal of the acid is difficult, thereby making it difficult to perfectly eliminating the irritating-smell even if cleaning is carried out repeatedly with great care by using a suitable solvent.

Moreover in the case where the carboxylic group in the phosphorus-containing dicarboxylic acid is used for the purpose of reacting with an other functional group, residual carboxylic group in the saturated aliphatic monocarboxylic acid reacts in the same manner as above, and for instance, when the carboxylic group is used as comonomer for polyester, there is a fear of causing the problem of unreasonably lowering the molecular weight of the objective polyester.

In such circumstances, there has eagerly been desired the development of a process for producing a highly pure phosphorus-containing carboxylic acid in high yield which process can facilitate industrial reaction control at a relatively low temperature and can also facilitate solvent removal.

DISCLOSURE OF THE INVENTION

Much attention, which has been paid to the above-mentioned problems with the prior arts, led to the accomplishment of the present invention. Thus an object of the present invention is to provide a phosphorus-containing carboxylic acid derivative which is excellent in solubility in an organic solvent, compatibility with a variety of synthetic resins and storage stability and which can exert excellent characteristics such as flame retardancy and the like; a process for producing the above-mentioned derivative; and usage such as a flame retardant.

Another object of the present invention is to provide a process which is capable of producing in high yield, a highly pure odor-free phosphorus-containing dicarboxylic acid being one of raw materials for a phosphorus-containing carboxylic acid derivative at a low reaction temperature as compared with prior arts, and also capable of removing the heat generated upon reaction and at the same time, facilitating removal of a solvent used in the reaction.

In order to achieve the above-mentioned objects, the present inventors have accumulated intensive extensive research and investigation. As a results it has been found that the objects can be attained by providing a phosphorus-containing carboxylic acid derivative having specific structure, a resin composition using the same, a resin molded article and a process for producing the aforesaid phosphorus-containing carboxylic acid derivative.

That is to say, the present invention pertains to the following:

[1] A flame retardant comprising as an effective ingredient, a phosphorus-containing carboxylic acid derivative which has a group containing phosphorus atom and has in its molecule, a group represented by the following formula (1):

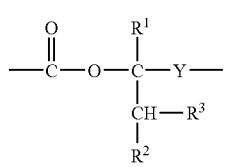

(1)

wherein $R^1$, $R^2$ and $R^3$ are each hydrogen atom or a hydrocarbon group having 1 to 18 carbon atoms, and Y is oxygen atom or sulfur atom.

[2] A phosphorus-containing carboxylic acid derivative which has a group containing phosphorus atom and has in its molecule, a group represented by the following formula (1):

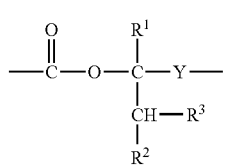

(1)

wherein $R^1$, $R^2$ and $R^3$ are each hydrogen atom or a hydrocarbon group having 1 to 18 carbon atoms, and Y is oxygen atom or sulfur atom.

[3] The phosphorus-containing carboxylic acid derivative as set forth in the preceding item [2] wherein the group represented by the formula (1) is a group represented by the following formula (2):

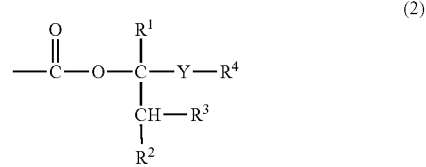

(2)

wherein $R^1$, $R^2$ and $R^3$ are each hydrogen atom or a hydrocarbon group having 1 to 18 carbon atoms, $R^4$ is a hydrocarbon group having 1 to 18 carbon atoms, $R^3$ and $R^4$ may be bonded to each other, and Y is oxygen atom or sulfur atom.

[4] The phosphorus-containing carboxylic acid derivative as set forth in the preceding item [2] wherein the group represented by the formula (1) is a group represented by the following formula (3):

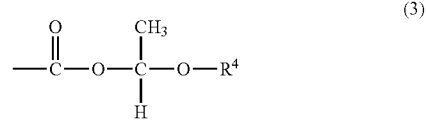

(3)

wherein $R^4$ is a hydrocarbon group having 1 to 18 carbon atoms.

[5] A polyhemiacetal type phosphorus-containing carboxylic acid derivative within the categories of the preceding item [2] comprises as a repeating unit, a group represented by the following formula (4):

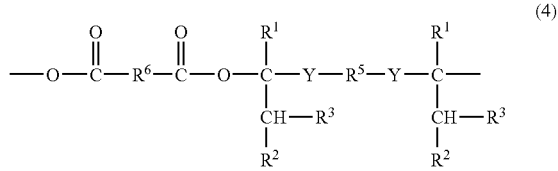

(4)

wherein $R^1$, $R^2$ and $R^3$ are each hydrogen atom or a hydrocarbon group having 1 to 18 carbon atoms, Y is oxygen atom or sulfur atom, $R^5$ is a bivalent organic group having 1 to 25 carbon atoms, and $R^6$ is a bivalent organic group which has 1 to 30 carbon atoms and comprises a group containing phosphorus atoms.

[6] The polyhemiacetal type phosphorus-containing carboxylic acid derivative as set forth in the preceding item [5] wherein the group represented by the formula (4) is a group represented by the following formula (5):

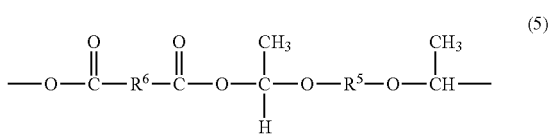

(5)

wherein $R^5$ is a bivalent organic group having 1 to 25 carbon atoms, and $R^6$ is a bivalent organic group which has 1 to 30 carbon atoms and comprises a functional group containing phosphorus atoms.

[7] A flame retardant comprises as an effective ingredient, the phosphorus-containing carboxylic acid derivative as set forth in any of the preceding items [2] to [6].

[8] A process for producing a phosphorus-containing carboxylic acid derivative as set forth in any of the preceding items [2] to [6] which comprises a step of reacting a phosphorus-containing carboxylic acid compound bearing both a carboxylic group and phosphorus atom with a vinyl ether compound, a vinyl thioether compound, a divinyl ether compound or a divinyl thioether compound.

[9] The process for producing a phosphorus-containing dicarboxylic acid derivative as set forth in the preceding item [8] wherein the phosphorus-containing carboxylic acid compound is produced by subjecting (A) a P—H group-containing phosphorus compound and (B) an unsaturated carboxylic acid each as a starting raw material to Michael addition reaction by (i) using acetonitrile or methoxypropyl acetate as a principal reaction solvent at (ii) a reaction temperature in the range of 50 to 150° C.

THE MOST PREFERRED EMBODIMENT TO CARRY OUT THE INVENTION

Figure 1:
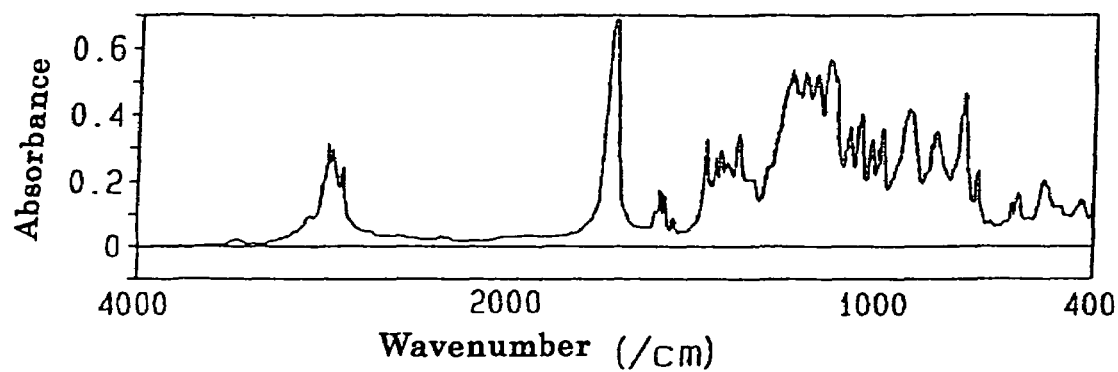
FIG. 1 is an infrared absorption spectrum of the product obtained in Example 1.

In the following, the present invention will be described in more detail.

The phosphorus-containing carboxylic acid derivative according to the present invention has a group containing phosphorus atom and a group represented by the following formula (1):

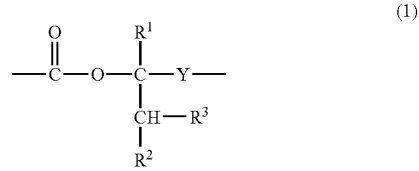

(1)

wherein $R^1$, $R^2$ and $R^3$ are each hydrogen atom or a hydrocarbon group having 1 to 18 carbon atoms, and Y is oxygen atom or sulfur atom.

The group represented by the formula (1) is exemplified, for instance, by the group represented by the following formula (2):

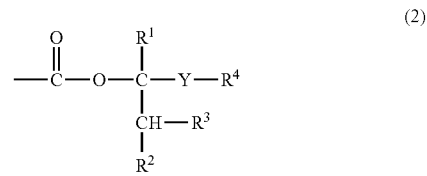

(2)

wherein $R^1$, $R^2$ and $R^3$ are each hydrogen atom or a hydrocarbon group having 1 to 18 carbon atoms, $R^4$ is a hydrocarbon group having 1 to 18 carbon atoms, $R^3$ and $R^4$ may be bonded to each other, and Y is oxygen atom or sulfur atom.

It is possible in the present invention to use as the group represented by the aforesaid formula (1) or (2), the group represented by the following formula (6):

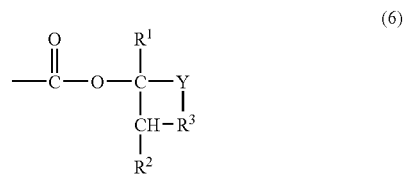

(6)

wherein $R^1$ and $R^2$ are each hydrogen atom or a hydrocarbon group having 1 to 18 carbon atoms, $R^3$ is a hydrocarbon group having 1 to 18 carbon atoms, and Y is oxygen atom or sulfur atom.

The group represented by the foregoing formula (1) is further exemplified by the group represented by the following formula (3):

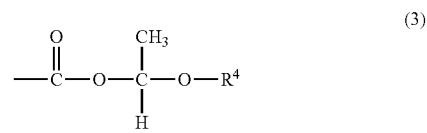

(3)

wherein $R^4$ is a hydrocarbon group having 1 to 18 carbon atoms.

The group represented by any of the formulae (1) to (3) and (6) is contained in 1 to 10 numbers, preferably 1 to 4 numbers per one molecule of the phosphorus-containing carboxylic acid derivative. The number of the above-mentioned group, when exceeding 10 per one molecule of the phosphorus-containing carboxylic acid derivative, sometimes gives rise to deterioration in the reactivity between the phosphorus-containing carboxylic acid and vinyl ether compound or vinyl thioether compound that are described hereinafter and also deterioration in compatibility of the phosphorus-containing carboxylic acid derivative with a synthetic resin.

In addition, the phosphorus-containing carboxylic acid derivative according to the present invention is exemplified by a hemiacetal type phosphorus-containing carboxylic acid derivative bearing the repeating unit represented by the following formula (4):

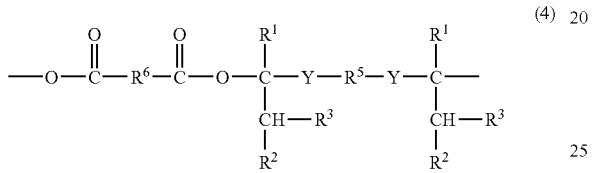
(4)

wherein $R^1$, $R^2$ and $R^3$ are each hydrogen atom or a hydrocarbon group having 1 to 18 carbon atoms, Y is oxygen atom or sulfur atom, $R^5$ is a bivalent organic group having 1 to 25 carbon atoms, and $R^6$ is a bivalent organic group which has 1 to 30 carbon atoms and comprises a group containing phosphorus atom.

Of the above-mentioned groups, the group represented by the following formula (5) is preferable:

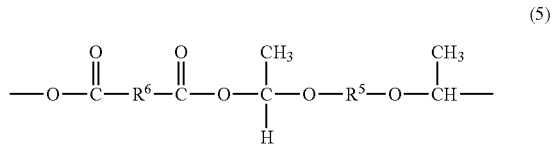
(5)

wherein $R^5$ is a bivalent organic group having 1 to 25 carbon atoms, and $R^6$ is a bivalent organic group which has 1 to 30 carbon atoms and comprises a functional group containing phosphorus atom.

The phosphorus-containing carboxylic acid derivative having the group represented by the above-mentioned formula (4) or formula (5) is exemplified by a phosphorus-containing polyhemiacetal resin having the aforesaid group as a repeating unit.

The weight average molecular weight of the above-mentioned phosphorus-containing polyhemiacetal resin is not specifically limited, but is usually in the range of 500 to 200,000, preferably in the range of 1,000 to 100,000.

As the phosphorus atom-containing group, use is made of the group in which phosphorus atoms therein are contained in a proportion of preferably 2 to 25% by weight, more preferably 3 to 15% by weight in the phosphorus-containing carboxylic acid derivative. The content of the phosphorus atoms, when being less than 2% by weight, sometimes gives rise to difficulty in imparting high flame retardancy to a resin molded article which is obtained from the resin composition containing the phosphorus-containing carboxylic acid derivative, whereas the content thereof, when being more than 25% by weight, brings about a tendency to deteriorate the resin characteristics of the objective resin molded article.

It is preferable that the above-mentioned phosphorus atom-containing group be the group represented by any of the following formulae (7) to (10):

(7)

wherein $R^7$ is hydrogen atom or an organic group having 1 to 20 carbon atoms, $R^8$ is an organic group having 1 to 20 carbon atoms, and when both $R^7$ and $R^8$ are an organic group, they may be bonded to each other;

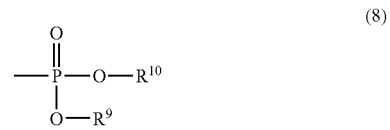
(8)

wherein $R^9$ and $R^{10}$ are each hydrogen atom or an organic group having 1 to 20 carbon atoms, and when both $R^9$ and $R^{10}$ are an organic group, they may be bonded to each other;

(9)

wherein $R^{11}$ and $R^{12}$ are each an organic group having 1 to 20 carbon atoms, and may be bonded to each other.

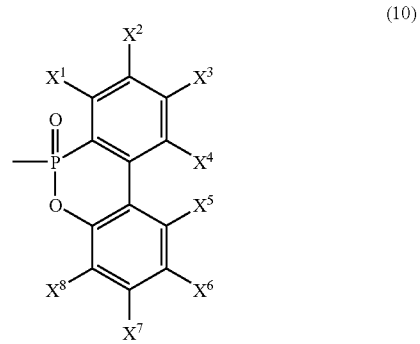
(10)

wherein $X^1$ to $X^8$, which are each an atom or group that may be the same as or different from one another, are each hydrogen atom, a halogen atom or a hydrocarbon group having 1 to 5 carbon atoms.

Examples of the phosphorus atom-containing group represented by the above-mentioned formula (9) include the group represented by any of the following formulae (11) and (12):

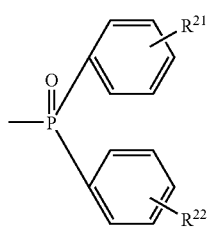

(11)

wherein $R^{21}$ and $R^{22}$ are each hydrogen atom or a hydrocarbon group having 1 to 12 carbon atoms.

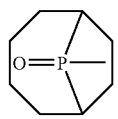

(12)

In addition, the benzene ring in the formula (ii) may contain a halogen atom such as chlorine and bromine.

Further, examples of the phosphorus atom-containing group represented by the above-mentioned formula (8) include the group represented by the following formula (13):

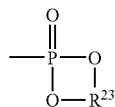

(13)

wherein $R^{23}$ is a hydrocarbon group having 1 to 40 carbon atoms.

In addition, $R^{10}$ in the formula (8) and $R^{23}$ in the formula (13) may contain a halogen atom such as chlorine and bromine.

In what follows, some description will be given of processes for producing the phosphorus-containing carboxylic acid derivative which has the chemical structure as described hereinbefore.

The phosphorus-containing carboxylic acid derivative is produced, as represented by the following reaction formula, by allowing a phosphorus-containing compound bearing both a carboxylic group and phosphorus atom to react (blocking) with a vinyl ether compound or a vinyl thioether compound. That is to say, the above-mentioned phosphorus-containing carboxylic acid derivative is obtained by allowing the carboxylic group of the phosphorus-containing compound to react with the vinyl group of the vinyl ether compound or of the vinyl thioether compound. Since it is comparatively easy to proceed with the reaction, the phosphorus-containing carboxylic acid derivative is obtained in high yield.

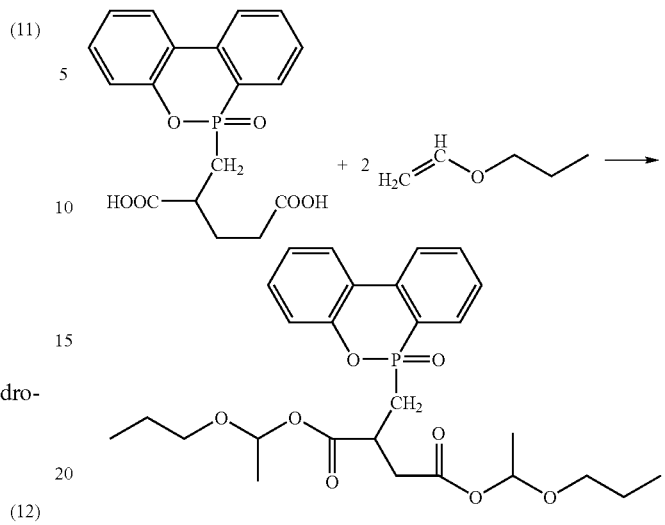

Being equilibrium reaction, the reaction is accelerated by the use of the vinyl ether compound or vinyl thioether compound in an amount somewhat larger than that of the phosphorus-containing carboxylic acid, thereby enhancing the yield thereof. Specifically it is desirable that the molar equivalent ratio of the vinyl group of the vinyl ether compound or vinyl thioether compound to the carboxylic groups of the phosphorus-containing carboxylic acid {molar equivalent ratio (vinyl group/carboxylic group)} be set on 1/1 to 2/1. When the molar ratio thereof exceeds 2/1, it is sometimes made impossible to raise the reaction temperature and further proceed with the reaction and at the same time, the production cost is unreasonably increased. In such a case, the molar equivalent ratio may be set on 0.5/1 to 1/1.

Examples of the phosphorus-containing carboxylic acid include that represented by any of the following formulae (14) and (15). There is also usable the phosphorus-containing carboxylic acid obtainable by allowing an unsaturated carboxylic acid such as acrylic acid or itaconic acid or an acid anhydride such as trimellitic anhydride to react with any of various phosphorus-containing compound:

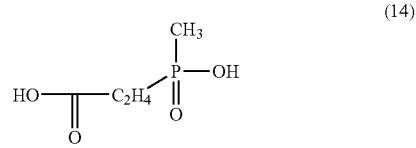

(14)

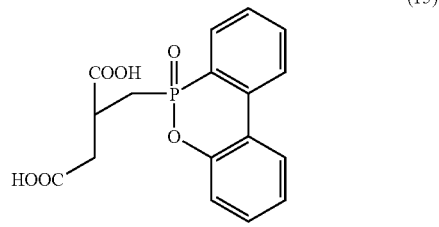

(15)

In particular, the compound is useful which is obtainable by allowing a carboxylic acid bearing unsaturated group such as itaconic acid to react with the phosphorus-containing compound represented by the following formula (16):

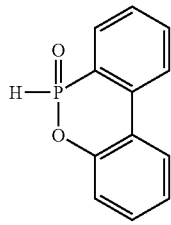

(16)

The content of the phosphorus atoms in the phosphorus-containing carboxylic acid is preferably 3 to 30% by weight, more preferably 5 to 20% by weight. The content thereof, when being less than 3% by weight, sometimes leads to difficulty in imparting high flame retardancy to a molded article obtained by molding a synthetic resin composition containing the phosphorus-containing carboxylic acid, whereas the content thereof, when being more than 30% by weight, brings about the tendency to markedly deteriorate the characteristics inherent in a molded article. The vinyl ether compound and vinyl thioether compound that are to be used in the production process according to the present invention mean the compound represented by the following formula (17):

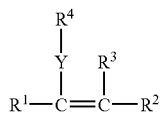

(17)

wherein $R^1$, $R^2$ and $R^3$ are each hydrogen atom or a hydrocarbon group having 1 to 18 carbon atoms, $R^4$ is a hydrocarbon group having 1 to 18 carbon atoms, and Y is oxygen atom or sulfur atom. Among them, usable is the cyclic compound represented by the following formula (18):

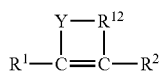

(18)

wherein $R^1$ and $R^2$ are each hydrogen atom or a hydrocarbon group having 1 to 18 carbon atoms, $R^{12}$ is a hydrocarbon group having 1 to 18 carbon atoms, and Y is oxygen atom or sulfur atom.

That is to say, the compound represented by the formula (18) is a cyclic vinyl ether compound such as a heterocyclic compound that bears one vinyl type double bond and in which oxygen atoms or sulfur atoms constitute heteroatoms.

Specific examples of the compound represented by any of the formulae (17) and (18) include aliphatic monovinyl ether compounds such as methylvinyl ether, ethylvinyl ether, isopropylvinyl ether, n-propylvinyl ether, n-butylvinyl ether, isobutylvinyl ether, tert-butylvinyl ether, 2-ethylhexylvinyl ether and cyclohexylvinyl ether; aliphatic monovinyl thioether compounds corresponding to the above-mentioned ether compounds, respectively; cyclic monovinyl ether compounds such as 2,3-dihydrofuran, 3,4-dihydrofuran, 2,3-dihydro-2H-pyran, 3,4-dihydro-2H-pyran, 3,4-dihydro-2-methoxy-2H-pyran, 3,4-dihydro-4,4-dimethyl-2H-pyran-2-on, 3,4-dihydro-2-ethoxy-2H-pyran and 3,4-dihydro-2H-pyran-2-sodium carboxylate; cyclic monovinyl thioether compounds corresponding to the ether compounds just mentioned.

The phosphorus-containing polyhemiacetal resin having the group represented by any of the above-mentioned formulae (4) and (5) as the repeating unit is produced by allowing a phosphorus-containing dicarboxylic acid compound bearing both two carboxylic groups and phosphorus atom to react with a divinyl ether compound (this process is sometimes referred to as blocking), as represented by the following reaction formula:

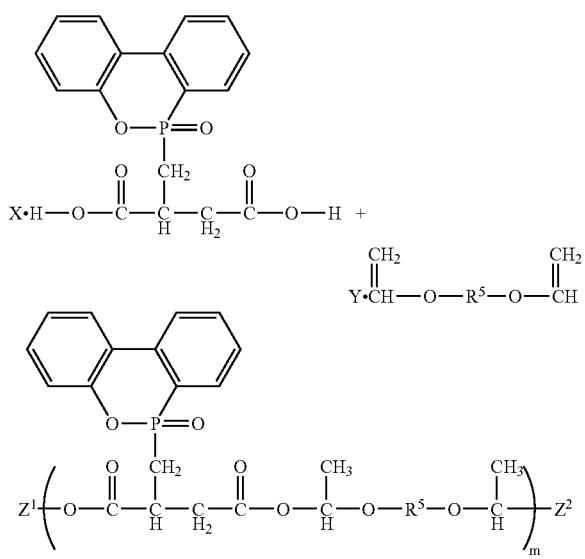

17

In the foregoing reaction formula, $R^5$ is a bivalent organic group having 1 to 25 carbon atoms, m is an integer from 2 to 20, X and Y are each the number of moles of the starting raw materials, respectively wherein X/Y=1/2 to 2/1, $Z^1$ and $Z^2$ are each a residual group of reaction terminal derived from the divinyl ether and dicarboxylic acid.

In the above-mentioned process, the phosphorus-containing dicarboxylic acid compound may be blended with a phosphorus-atom-free dicarboxylic acid compound so that the resultant blend is reacted with the divinyl ether compound.

Since the reaction is polymerization addition reaction, it is possible to adjust the molecular weight of the objective resin by controlling the blending ratio of the dicarboxylic acid compound to the divinyl ether. Moreover, the dicarboxylic acid compound and divinyl ether compound as starting raw materials may be collectively fed to the reaction system to proceed with the reaction. Alternatively, they may be separately fed respectively. For instance, the divinyl ether compound may be added dropwise to the dicarboxylic acid compound. In this case, any of the above-mentioned phosphorus-containing dicarboxylic acid, phosphorus-free dicarboxylic acid and divinyl ether compound may be used alone or in combination with at least one other.

Examples of the aforesaid phosphorus-containing dicarboxylic acid include the compound represented by the above-mentioned formula (15). Also usable is the phosphorus-containing carboxylic acid obtainable by allowing an unsaturated dibasic carboxylic acid such as itaconic acid or an acid anhydride such as trimellitic anhydride to react with any of various phosphorus-containing compound.

In particular, the compound is useful which is obtainable by allowing a carboxylic acid bearing an unsaturated group such as itaconic acid to react with the phosphorus-containing compound represented by the foregoing formula (16).

In the case where use is made of the group represented by any of the above-mentioned formulae (4) and (5) as the repeating unit, the group may be used alone or in combination with at least one other or may be incorporated with a repeating unit other than the repeating unit represented by any of the formulae (4) and (5). The resin contains the repeating unit represented by any of the formulae (4) and (5) in an amount of usually at least 10% by weight, preferably at least 20% by weight, particularly at least 50% by weight when used as a flame retardant.

The resin obtainable in the foregoing manner has the chemical structure represented by the following formula (19):

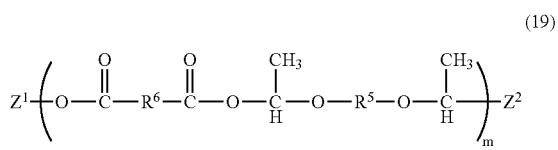

(19)

wherein $R^5$ and $R^6$ are each as previously defined, and $Z^1$ and $Z^2$ are each hydrogen atom or the group represented by any of the following formulae (20), (21) and (22):

(20)

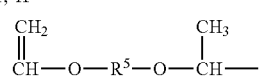

(21)

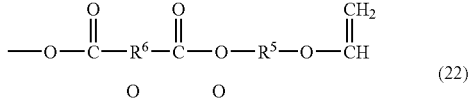

(22)

wherein $R^5$ and $R^6$ are each as previously defined.

The content of phosphorus atoms in the phosphorus-containing polyhemiacetal resin is preferably 2 to 25% by weight, more preferably 3 to 15% by weight. The content thereof, when being less than 2% by weight, sometimes leads to difficulty in imparting high flame retardancy to a resin molded article obtained from a resin composition containing the phosphorus-containing polyhemiacetal resin, whereas the content thereof, when being more than 25% by weight, brings about the tendency to deteriorate the resin characteristics of the resin molded article.

Examples of the phosphorus atom-free dicarboxylic acid compound include aliphatic dicarboxylic acid having 2 to 25 carbon atoms such as maleic acid, fumaric acid, mesaconic acid, citraconic acid, itaconic acid, chlorinated maleic acid, HET acid, succinic acid, adipic acid, azelaic acid sebacic acid and decamethylene dicarboxylic acid; aromatic dicarboxylic acid such as phthalic acid, isophthalic acid, terephthalic acid, dichlorophthalic acid, tetrachlorophthalic acid, tetrachloroisophthalic acid and tetrachloroterephthalic acid; alicyclic dicarboxylic acid such as tetrahydrophthalic acid, hexahydrophthalic acid, methylhexahydrophthalic acid, hexahydroisophthalic acid and hexahydroterephthalic acid.

In addition, examples of the phosphorus atom-free dicarboxylic acid compound include a dicarboxylic acid compound half ester body which is obtained by addition reaction of one mol of a diol and 2 moles of an acid anhydride in place of the dicarboxylic acid compound. Examples of such diol include ethylene glycol, diethylene glycol, 1,2-propylene glycol, 1,3-propylene glycol, 1,3-butalnediol, 1,4-butanediol, 2,3-butanediol, 1,6-hexanediol, pentanediol, dimethylbutanediol, hydrogenated bisphenol A, bisphenol A, hydrogenated bisphenol F, bisphenol F, neopentyl glycol, 1,8-octanediol, 1,4-cyclohexane dimethanol and 2-methyl-1,3-propanediol. Examples of the acid anhydride which is used for the half ester body include an acid anhydride from a dicarboxylic acid such as succinic acid, glutaric acid, phthalic acid, maleic acid, dichlorophthalic acid, tetrachlorophthalic acid, tetrahydrophthalic acid, hexahydrophthalic acid and methylhexahydrophthalic acid.

Specific examples of the divinyl ether compound to be used for the production of the phosphorus-containing polyhemiacetal resin according to the present invention include trimethylene glycol divinyl ether, triethylene glycol divinyl ether (TEGDVE), 1,4-bisvinyloxymethylcyclohexene, ethylene glycol divinyl ether, polyethylene glycol divinyl ether, 1,4-butanediol divinyl ether (1,4BDVE), pentanediol divinyl ether, hexanediol divinyl ether, 1,4-cyclohexane dimethanol divinyl ether (CHDVE) and a thioether compound which corresponds to any of the above-exemplified divinyl ether compound.

The phosphorus-containing carboxylic acid derivative according to the present invention is obtainable by allowing the above-mentioned phosphorus-containing carboxylic acid to react with the vinyl ether compound, vinyl thioether compound, vinyl thioether compound or divinyl thioether compound at a temperature in the range of room temperature to 150° C. It is possible in this case to use an acid catalyst for the purpose of accelerating the reaction. Examples of such catalyst include an acidic phosphoric acid ester compound represented by the following formula (23):

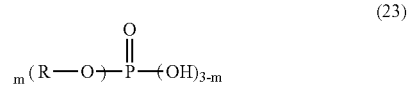

(23)

wherein R is an alkyl group having 3 to 10 carbon atoms, a cycloalkyl group or an aryl group, and m is 1 or 2.

Specific examples of the acidic phosphoric acid ester compound represented by the above-mentioned formula (23) include phosphoric acid monoester and phosphoric acid diester each of a primary alcohol such as n-propanol, n-butanol, n-hexanol, n-octanol and 2-ethylhexanol, and secondary alcohol such as isopropanol, 2-butanol, 2-hexanol, 2-octanol and cyclohexanol.

Moreover, an organic solvent may be used for the purpose of uniformizing the reaction system and at the same time, facilitating the reaction. Examples of such organic solvent include aromatic hydrocarbons such as benzene, toluene, xylene, ethylbenzene, aromatic petroleum naphtha, tetralin, turpentine oil, Solvesso # 100 (trade name available from Exxon Chemical Co., Ltd.) and Solvesso #150 (trade name available from Exxon Chemical Co., Ltd.); ethers such as dioxane and tetrahydrofuran; esters and ether esters such as methyl acetate, ethyl acetate, n-propyl acetate, isopropyl acetate, n-butyl acetate, isobutyl acetate, sec-butyl acetate, amyl acetate, methoxybutyl acetate and methoxypropyl acetate (PMAc); ketones such as acetone, methyl ethyl ketone, methyl isobutyl ketone, methyl amyl ketone, cyclohexanone, isophorone, mesitil oxide, methyl isoamyl ketone, ethyl-n-butyl ketone, ethyl amyl ketone, diisobutyl ketone, diethyl ketone, methyl propyl ketone and diisobutyl ketone; phosphoric acid esters such as trimethyl phosphate, triethyl phosphate and tributyl phosphate; nitrogen-containing compound such as N,N-dimethylformamide, N,N-dimethylacetoamide, N-methyl-2-pyrrolidone, N-methylmorpholine and acetonitrile; and dimethylsulfoxide.

One of the objects of the present invention is to provide a process capable of producing a highly pure odorless phosphorus-containing carboxylic acid, especially phosphorus-containing dicarboxylic acid in high yield at a low reaction temperature as compared with a conventional temperature, while enabling removal of heat generated upon reaction and facilitating solvent removal, said carboxylic acid being a starting raw material for the phosphorus-containing carboxylic acid derivative.

As mentioned hereinbefore, Michael addition reaction has heretofore been thought to proceed only under a high reaction temperature in the range of 160 to 250° C. However, as the result of intensive extensive research and investigation made by the present inventors on the addition reaction between similar phosphorus compound and C=C double bond of an unsaturated aliphatic carboxylic acid, it has been discovered that the aforesaid reaction proceeds at a comparatively low reaction temperature in the range of 50 to 150° C. under a specific reaction conditions, and it has been found out that Michael addition reaction proceeds by the use of acetonitrile or methoxypropyl acetate as a solvent for the aforesaid reaction. That is to say, the present invention also provides a process for producing a phosphorus-containing carboxylic acid compound which comprises subjecting (A) a P—H group-containing phosphorus compound and (B) an unsaturated carboxylic acid each as a starting raw materials to Michael addition reaction by (i) using acetonitrile or methoxypropyl acetate as a principal reaction solvent at (ii) a reaction temperature in the range of 50 to 150° C. The above-mentioned process is preferably used for the production of a phosphorus-containing carboxylic acid to be used as a starting raw material in the case of producing the phosphorus-containing carboxylic acid derivative according to the present invention.

In the above-described production process, the component (A) as the starting raw material is the compound represented by the following formula (24):

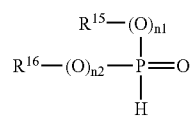

(24)

wherein $R^{15}$ and $R^{16}$ are each hydrogen atom or a same or different organic group having 1 to 20 carbon atoms which may be bonded to each other to form a ring, and n1 and n2 are each independently 0 or 1; the component (B) as the starting raw material is fumaric acid, maleic acid or itaconic acid each represented by the following formula (25):

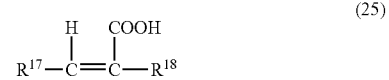

(25)

wherein $R^{17}$ is hydrogen atom or —COOH group, when $R^{17}$ is hydrogen atom, $R^{18}$ is —CH$_2$COOH group, and when $R^{17}$ is —COOH group, $R^{18}$ is hydrogen atom; and the product is represented by the following formula (26):

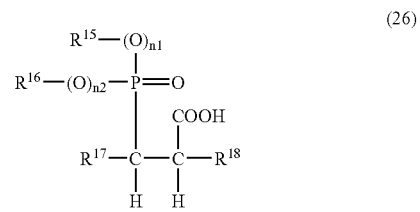

(26)

wherein $R^{15}$, $R^{16}$, $R^{17}$, $R^{18}$ n1 and n2 are the same as defined in the foregoing description.

In the formula (24), $R^{15}$ and $R^{16}$ may be same or different organic group having 1 to 20 carbon atoms which is exemplified by methyl group, ethyl group, n-propyl group, isopropyl group, n-butyl group, isobutyl group, sec-butyl group, tert-butyl group, n-hexyl group, iso-hexyl group, n-heptyl group, isoheptyl group, n-octyl group, isooctyl group, n-dodecyl group, isododecyl group, n-octadecyl group, iso-octadecyl group, cyclopentyl group, cyclohexyl group, phenyl group, benzyl group and the like, and $R^{15}$ and $R^{16}$ may be bonded to each other.

The P—H group-containing phosphorus compound as the component (A) is preferably exemplified by 9,10-dihydro-9-oxa-10-phosphaphenanthrene-10-oxide represented by the foregoing formula (16) or diphenylhydrogen phosphite for excellent water resistivity of the phosphorus-containing dicarboxylic acid as the product after the reaction, and also exemplified by diethylhydrogen phosphite for excellent weather resistance.

The unsaturated carboxylic acid as the component (B) is exemplified by acrylic acid, methacrylic acid, mesaconic acid, citraconic acid, cyclohexanecarboxylic acid, fumaric acid, maleic acid or itaconic acid. Of these, fumaric acid, maleic acid and itaconic acid are preferable.

The acetonitrile as the solvent has a boiling point of about 81° C., and the methoxypropyl acetate has a boiling point of about 146° C., in which reagent grade solvent and industrial grade solvent are both usable.

The reaction atmosphere includes atmospheric pressure or pressurized pressure, and a reaction temperature in the range of 50 to 150° C., preferably 60 to 150° C. The reaction temperature, when being lower than 50° C., requires an unreasonably long reaction time, whereas the temperature, when being higher than 150° C., brings about an anxiety of fierce coloring of the objective product.

The reaction is that termed Michael addition reaction between P—H group of the phosphorus compound and C=C double bonds of an unsaturated carboxylic acid, and is represented as the following:

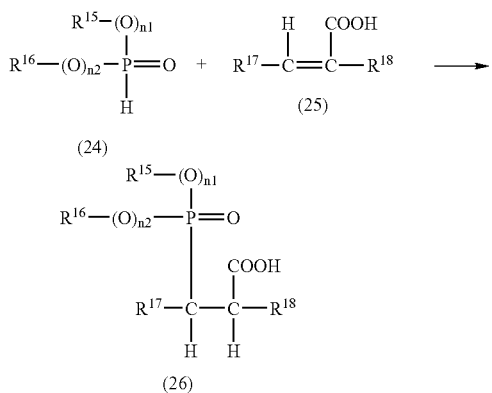

wherein $R^{15}$, $R^{16}$, $R^{17}$, $R^{18}$, n1 and n2 each are the same as previously defined.

Acetonitrile and methoxypropyl acetate are each a solvent having high general-purpose properties, and solubilize the phosphorus compound and unsaturated dicarboxylic acid. However, much of the phosphorus-containing dicarboxylic acids as the product are insoluble in acetonitrile and methoxypropyl acetate and thus, it is possible to purify the product from the starting raw materials only by filtration after the reaction. In the case of completely removing residual acetonitrile, removal thereof under vacuum is facilitated, since it has a boiling point of about 80° C. under atmospheric pressure.

It is known that the reaction is exothermic. The heat generated upon the reaction has hitherto been the cause of uncontrollable sudden temperature rise in this reaction. Nevertheless it is possible for the process according to the present invention to suppress the uncontrollable sudden temperature rise by proceeding with the reaction under reflux at a temperature lower than in the prior arts, since the boiling points under atmospheric pressure of acetonitrile and methoxypropyl acetate are respectively about 80° C. and about 146° C. In addition, the reaction under comparatively low temperature makes it possible to obtain phosphorus-containing dicarboxylic acid without unfavorable coloring.

It is possible for the above-described reaction to suppress the reaction temperature to a lower level than 50 to 150° C. in the prior arts. However in the case of carrying out the reaction at 84 to 150° C., reaction under a pressurized pressure is necessary because of acetonitrile having a boiling point of about 80° C. under atmospheric pressure.

In the foregoing reaction, acetonitrile or methoxypropyl acetate, which is used as a solvent, may be used in combination with an other organic solvent for the purpose of regulating the boiling point thereof, viscosity thereof, solubility of starting raw materials and the like. Examples of such solvent include aromatic hydrocarbons such as benzene, toluene, xylene, ethylbenzene, aromatic petroleum naphtha, tetralin, turpentine oil, Solvesso # 100 (trade name; available from Exxon Chemical Co., Ltd.) and Solvesso # 150 (trade name; available from Exxon Chemical Co., Ltd.); ethers such as dioxane and tetrahydrofuran; esters and ether esters such as methyl acetate, ethyl acetate, n-propyl acetate, isopropyl acetate, n-butyl acetate, isobutyl acetate, tert-butyl acetate, amyl acetate, methoxybutyl acetate and methoxypropyl acetate (PMAc); ketones such as acetone, methyl ethyl ketone, methyl isobutyl ketone, methyl amyl ketone, cyclohexanone, isophorone, mesitil oxide, methyl isoamyl ketone, ethyl-n-butyl ketone, ethyl amyl ketone, diisobutyl ketone, diethyl ketone, methyl propyl ketone and diisobutyl ketone; phosphoric acid esters such as trimethyl phosphate, triethyl phosphate and tributyl phosphate; dimethylsulfoxide; and N,N-dimethylformamide.

The above-exemplified solvent other than the acetonitrile and methoxypropyl acetate is added in an amount of preferably at most 60% by weight based on the whole amount of the solvents, and when added by more than 60% by weight based thereon, sometimes leads to failure to assure the working effect of the present invention.

In the above-mentioned reaction, the amount of the acetonitrile or methoxypropyl acetate is preferably 10 to 80% by weight based on the total feed amount, particularly preferably 20 to 60% by weight based thereon. The amount of the acetonitrile or methoxypropyl acetate, when being less than 10% by weight based thereon, sometimes brings about deterioration in reactivity due to excessively high viscosity of the reaction system, and difficulty in solubilizing at room temperature, the phosphorus compound and unsaturated dicarboxylic acid that are each an unreacted starting raw material, thereby deteriorating the refining efficiency, whereas the aforesaid amount, when being more than 80% by weight based thereon, sometimes leads not only to necessity for a long time in solvent removal, but also to lowered rate of reaction accompanying a decrease in the concentration of the reactants.

In the above-mentioned reaction, the molar feed ratio of the phosphorus compound/unsaturated dicarboxylic acid, which is indicated by the equivalent ratio of P—H group/double bond, is usually set in the range of preferably 1/0.5 to 1/2. The molar feed ratio thereof, when being more than 1/0.5, in other words, excessive phosphorus compound, results in a large amount of residual phosphorus compound after the completion of the reaction, thus needing a large amount of the acetonitrile or methoxypropyl acetate upon refining. On the contrary, The molar feed ratio thereof, when being less than 1/2, in other words, excessive unsaturated dicarboxylic acid, results in a large amount of residual unsaturated dicarboxylic acid after the completion of the reaction, thus needing a large amount of the acetonitrile or methoxypropyl acetate upon refining.

The above-mentioned reaction proceeds even in the absence of a catalyst, however for the purpose of accelerating the reaction, an acid catalyst, base catalyst, metal complex catalyst or radical generating agent is usable. A mixed catalyst by the combination thereof may also be used.

Examples of the acid catalyst as mentioned above include an acidic phosphoric acid ester compound represented by the foregoing formula (23).

Specific examples of the acidic phosphoric acid ester compound represented by the formula (23) include phosphoric acid monoester and phosphoric acid diester each of a primary alcohol such as n-propanol, n-butanol, n-hexanol, n-octanol and 2-ethylhexanol, and secondary alcohol such as isopropanol, 2-butanol, 2-hexanol, 2-octanol and cyclohexanol. A preferable example thereof is 2-ethylhexyl acid phosphate "AP-8" (trade name, available from Daihachi Chemical Industry Co., Ltd.) represented by the following formula (27):

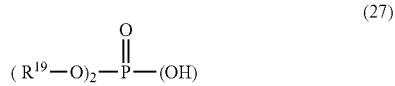

(27)

wherein R[19] is 2-ethylhexyl group.

The base catalyst as mentioned above is exemplified by, but is not limited to, monoamines, diamines, triamines, polyamines, cyclic amines, alcohol amines and ether amines, and is specifically exemplified by triethylamine; N,N-dimethylcyclohexylamine; N,N,N',N'-tetramethylethylenediamine; N,N,N',N'-tetramethylpropane-1,3-diamine; N,N,N',N'-tetramethylhexane-1,6-diamine; N,N,N',N'',N''-pentamethyldiethylenetriamine; N,N,N',N'',N''-pentamethyldipropylenetriamine; tetramethylguanidine; N,N-di(polyoxyethylene)stearylamine; N,N-di(polyoxyethylene)beeftallow-amine; triethylenediamine; N,N'-dimethylpiperazine; N-methyl-N'-(2-dimethylamino)-ethylpiperazine; N-methylmorpholine; 1,8-diazabicyclo[5.4.0]undece-7-ene; pyridine; N-ethylmorpholine; N—(N',N'-dimethylaminoethyl)-morpholine; 1,2-dimethylimidazole; dimethylaminoethanol; dimethylaminoethoxyethanol; N,N,N'-trimethylaminoethylethanolamine; N-methyl-N'-(2-hydroxyethyl)-piperazine; N-(2-hydroxyethyl)-morpholine; bis(2-dimethylaminoethyl) ether; ethylene glycol bis-(3-dimethylaminopropyl) ether. Of these, pyridine and 1,8-diazabicyclo[5.4.0]undece-7-ene are preferable.

An organometal complex in which an organic ligand is coordinated in a central metal exemplifies the above-mentioned metal complex catalyst. Examples of the central metal include iron, nickel, cobalt, ruthenium, rhodium, palladium, platinum and iridium. Of these, ruthenium, rhodium, palladium and platinum are preferable, and palladium is more preferable.

There are usable metal complexes having any of a variety of structures, of which a metal complex having so called a low valency is suitable. In particular, a metal complex having zero valency is preferable which contains a tertiary phosphine or a tertiary phosphite as a ligand. Moreover it is also preferable to use a precursory complex which can easily be converted in the reaction system, into palladium complex having zero valency. It is also a preferable embodiment to adopt a method which comprises mixing in the reaction system, a metal complex which does not contain a tertiary phosphine or a tertiary phosphite as a ligand and a tertiary phosphine or a tertiary phosphite, thus generating a palladium complex having zero valency which contains the tertiary phosphine or tertiary phosphite as a ligand, and using the aforesaid palladium complex as such. Examples of the ligand that exhibits an advantageous performance in any of the above-mentioned methods include a variety of tertiary phosphines and tertiary phosphites. Preferably usable ligands are exemplified by triphenylphosphine, diphenylmethylphosphine, phenyldimethyl phosphine, trimethylphosphine, triethylphosphine, diphenylcyclohexylphosphine, phenyldicyclohexylphosphine, 1,4-bis(diphenylphosphino)butane, trimethylphosphite and triphenylphosphite. The metal complex which does not contain a tertiary phosphine or a tertiary phosphite as a ligand and which is used in combination with any of them is exemplified by, but is not limited to bis(benzylideneacetone) palladium and palladium acetate. Preferably usable complex of a phosphine or phosphite is exemplified by dimethylbis(triphenylphosphine)palladium, dimethylbis(diphenylmethylphosphine) palladium {abbreviated to cis-PdMe$_2$ (P.ph$_2$.Me)$_2$}, dimethylbis(triethylphosphine)palladium, (ethylene)bis(triphenylphosphine) palladium and tetrakis(triphenylphosphine) palladium. In addition, there may be used as such a complex having two valencies such as palladium which has been treated with a reducing agent such as butyllithium. More preferable example thereof is dimethylbis(diphenylmethylphosphine) palladium {abbreviated to cis-PdMe$_2$(P.ph$_2$.Me)$_2$}.

Examples of the above-mentioned radical generating agent include diacyl peroxides such as acetyl peroxide, isobutyl peroxide, octanoyl peroxide and decanoyl peroxide; diisopropyl peroxydicarbonate and di-2-ethylhexyl peroxydicarbonate; peroxy esters such as tert-butyl peroxyisobutyrate, tert-butyl perpivalate and 1,1,3,3-tetrabutyl peroxy-2-ethylhexanoate; and azobis such as 2,2'-azobis(2-methylpropylnitrile), 2,2'-azobis(2, 4-dimethylvaleronitrile) and dimethyl-2,2'-azobis(2-methylpropionate. Preferable example thereof is 1,1,3,3-tetrabutyl peroxy-2-ethylhexanoate.

Optimum reaction time, which is different depending on starting raw species and presence/absence of a catalyst, is 1 to 16 hours. A reaction time of less than one hour leads to lowered production efficiency of a phosphorus-containing dicarboxylic acid.

The novel process for producing the above-described phosphorus-containing dicarboxylic acid makes it possible to refine both the product and starting raw material only by means of filtration after the reaction through the use of acetonitrile or methoxypropyl acetate each having high general-purpose properties, and easily refine the residual acetonitrile or methoxypropyl acetate as the solvent by means of vacuum removal in the case of completely removing the solvent, whereby highly pure objective product is obtained.

Further, the process for producing the above-described phosphorus-containing dicarboxylic acid is capable of proceeding with the reaction at a low temperature as compared with the prior arts, whereby white phosphorus-containing dicarboxylic acid is obtainable in high yield.

Furthermore, the process for producing the above-described phosphorus-containing dicarboxylic acid enables to suppress uncontrollable sudden temperature rise by proceeding with the reaction at a low temperature as compared with the prior arts, proceed with the reaction under reflux, since the boiling points of the acetonitrile and methoxypropyl acetate are about 80° C. and 146° C., respectively.

The phosphorus-containing dicarboxylic acid derivative according to the present invention, when being heated or irradiated with activation energy beam such as ultraviolet ray or electron beam, causes elimination of a vinyl ether compound, vinyl thioether compound, divinyl ether compound or divinyl thioether compound, thus enabling to regenerate the original carboxylic groups (deblocking). An acid catalyst accelerates this regeneration reaction of the free acid. Examples of the acid catalyst include protonic acid such as halogenocarboxylic acid, sulfonic acid, monoester of sulfuric acid, monoester of phosphoric acid, diester of phosphoric acid, polyphosphoric acid ester, monoester of boric acid and diester of boric acid; and Lewis acid such as boron fluoride (BF$_3$), ferric chloride (FeCl$_3$), stannic chloride (SnCl$_4$), aluminum chloride (AlCl$_3$) and zinc chloride (ZnCl$_2$). There is also available as a photoacid catalyst, Adeka Optomer Sp series (trade name; available from Asahi Denka Industrial Co., Ltd.).

The phosphorus-containing carboxylic acid derivative to be obtained in the aforesaid manner is utilized also as a curing agent for various synthetic resins each having a reactive functional group. The carboxylic group regenerated after deblocking rapidly reacts with a reactive functional group of a synthetic resin, whereby flame-retardative cured synthetic resin is easily obtained. Examples of the reactive functional groups include epoxy group, silanol group, alkoxysilane group, hydroxyl group, amino group, imino group, isocyanate group, blocked isocyanate group, cyclocarbonate group, vinyl ether group, vinyl thioether group, aminomethylol group, alkylatd aminomethylol group, acetal group and ketal group. Examples of the synthetic resin having such reactive functional group include epoxy group-containing compound such as epoxy resin of bisphenol A type, epoxy resin of bisphenol F type, epoxy resin of cresol novolak type, epoxy group-modified silicone resin, epoxy resin of phenol novolak type, alicyclic epoxy resin, homopolymer and copolymer of glycidyl(meth)acrylate or 3,4-epoxycyclohexylmethyl(meth)acrylate, polyglycidyl compound which is obtained by the reaction between polycarboxylic acid or polyol and epichlorohydrin; compounds such as the condensation product of the compound represented by the following formula (28):

$$(R^{20})_n Si(OR^{21})_{4-n} \qquad (28)$$

wherein $R^{20}$ and $R^{21}$ are each an alkyl group having 1 to 18 carbon atoms or an aryl group, and n is 0, 1 or 2, homopolymer and copolymer of α,β-unsaturated silane compounds such as acryloyloxypropyltrimethoxysilane, methacryloyloxypropyltrimethoxysilane and silane compounds such as acryloyloxypropyltrimethoxysilane, methacryloyloxypropyltrimethoxysilane and compounds each containing silanol group or alkoxysilane group exemplified by methacryloyloxypropyltri-n-buthoxysilane and a hydrolysis product of any of the above-cited compounds; hydroxy group-containing compounds such as aliphatic polyols, phenols, polyalkyleneoxy glycols, homopolymer and copolymer of an α,β-unsaturated compound such as 2-hydroxyethyl(meth)acrylate and 2-hydroxypropyl(meth)acrylate and an adduct of any of these polyols with ε-caprolactone; amino group-containing compound such as aliphatic and aromatic diamino compounds, polyamino compounds and polyamino compounds each being obtained by reducing cyanoethylation reaction product of the above-mentioned polyols; imino group-containing compounds such as aliphatic and aromatic polyimino compounds; isocyanate group-containing compounds such as p-phenylene diisocyanate, biphenyldiisocyanate, tolylenediisocyanate, 3,3'-dimethyl-4,4'-biphenylenediisocyanate, 1,4-tetramethylenediisocyanate, hexamethylenediisocyanate, 2,2,4-trimethylhexane-1,6-diisocyanate, methylenebis(phenylisocyanate), lysinemethylesterdiisocyanate, bis(isocyanateethyl)fumarate, isophoronediisocyanate, methylcyclohexyldiisocyanate, 2-isocyanateethyl-2,6-diisocyanate hexanoate, biuret thereof, isocyanurate thereof, an adduct compound of any of these isocyanates with the above-mentioned polyols; blocked isocyanate group-containing compounds such as a blocked product of any of the above-exemplified isocyanate group-containing compounds blocked with any of phenols, lactams, active methylenes, alcohols, acid amides, imides, amines, imidazoles, ureas, imines and oximes; cyclocarbonate group-containing compounds such as homopolymer and copolymer of 3-(meth)acryloyloxypropylene carbonate, polyvalent cyclocarbonate group-containing compounds obtained by the reaction between any of the epoxy group-containing compounds and carbon dioxide; compounds containing a vinyl ether group or vinyl thioether ether group such as polyvalent vinyl ether compounds obtained by the reaction between the aforesaid polyvalent hydroxyl group-containing compounds and halogenated alkylvinyl ether, polyvinyl ether compounds obtained by the reaction between hydroxyalkylvinyl ether and polyvalent carboxyl group-containing compound or the above-exemplified polyisocyanate compound, vinyl ether compounds exemplified by the copolymer of vinyloxyalkyl(meth)acrylate and an α,β-unsaturated compound, and vinyl thioether compounds each corresponding to any of the foregoing; compounds containing an aminomethylol group or alkylated aminomethylol group such as melamine-formaldehyde resin, glycolyl-formaldehyde resin, urea-formaldehyde resin, homopolymer and copolymer of an α,β-unsaturated compound containing an aminomethylol group or alkylated aminomethylol group; and compounds containing an acetal group or ketal group such as polyvalent ketones, polyvalent aldehyde compounds, polyvalent acetal compounds obtained by the reaction between the foregoing polyvalent vinyl ether compound and an alcohol or oxoacid ester, condensation product between any of them and a polyol compound, homopolymer and copolymer of an adduct of the vinyloxyalkyl(meth)acrylate with an alcohol or an oxoacid ester.

The resin composition according to the present invention comprises as indispensable ingredients, a synthetic resin bearing in its molecule, at least two reactive functional groups reactive with a carboxylic group, and the foregoing phosphorus-containing carboxylic acid derivative. Those which the synthetic resin possesses and which have already been described on the curing agent exemplify the reactive functional groups. The synthetic resin bearing in is molecule, at least two reactive functional groups reactive with a carboxylic group is exemplified by epoxy resin. The synthetic resin, which bears at least two reactive functional groups, forms crosslinked structure for the phosphorus-containing carboxylic acid derivative. The above-mentioned resin composition may be blended at need, with a curing agent, filler, pigment, coloring agent, plasticizer, catalyst, solvent and the like.

In the resin composition, the content of the carboxylic group after the deblocking of the phosphorus-containing carboxylic acid derivative is preferably 0.1 to 5.0 equivalents based on one equivalent of the reactive functional groups reactive with a carboxylic group, more preferably 0.2 to 3.0 equivalents. The content thereof, when being less than 0.1 equivalent, brings about markedly lowered phosphorus concentration in a resin molded article, thereby deteriorating the working effect on flame retardancy, coloring preventiveness and heat resistance, whereas the content thereof, when being more than 5.0 equivalents, gives rise to a tendency to deteriorate the mechanical properties of the resin molded article.

The content of the phosphorus atoms in the resin composition is preferably in the range of 0.1 to 15% by weight. The content thereof, when being less than 0.1% by weight, leads to failure in sufficiently exhibiting the functions such as heat resistance and flame retardancy, whereas the content thereof, when being more than 15% by weight, brings about deterioration in the properties inherent to the synthetic resin.

The above-mentioned phosphorus-containing carboxylic acid derivative is used as effective ingredients for a flame retardant, coloring preventive agent and heat resistance-imparting agent. In the case where the phosphorus-containing carboxylic acid derivative is used as a flame retardant, it is preferable that the content of the phosphorus atoms contained in the resin molded article (cured resin) produced by molding the resin composition be regulated to the range of 1.5 to 15% by weight. In the case, however, where an other flame retardant is used in combination, the content thereof even less than 1.5% by weight can exhibit the working effect. In the case where the phosphorus-containing carboxylic acid derivative is used as a coloring preventive agent, it is preferable that the content of the phosphorus atoms contained in the resin molded article be regulated to the range of 0.1 to 15% by weight. In the case where the phosphorus-containing carboxylic acid derivative is used as a heat resistance-imparting agent, it is preferable that the content of the phosphorus atoms contained in the resin molded article be regulated to the range of 1 to 15% by weight. The content thereof, when being less than each of the lower limits, unfavorably results in unrecognized improvement in flame retardancy, coloring preventiveness and heat resistance, whereas the content thereof, when being more than 15% by weight in any case, unfavorably leads to unreasonably high water absorption of the resin molded article.

Subsequently, curing the resin composition and molding the same into a predetermined shape obtain a resin-molded article. A curing method using a curing agent is usually adopted. The phosphorus-containing carboxylic acid derivative according to the present invention can function alone as a curing agent, but can be used in combination with another curing agent. Usable other curing agent is exemplified by any of the customarily used curing agents such as an acid anhydride, polyamine based compound and phenol based compound, and a compound produced by modifying a carboxylic acid with the compound bearing the group represented by the foregoing formula (8). The amount of the other curing agent to be used is limited to preferably at most 120% by weight based on the phosphorus-containing carboxylic acid derivative. When the amount thereof is 120% or more by weight, the content of the phosphorus atoms in the resin molded article is lowered, thereby sometimes causing a failure in obtaining the required flame retardancy.

According to the purpose of use, there is adopted as a method for molding the resin composition, cast molding method, injection molding method, extrusion molding method, vacuum molding method and compression molding method that have hitherto been used for molding a synthetic resin.

The resin-molded article (cured resin) produced by molding the resin composition becomes practical by adding the same to any of various synthetic resins. Examples of the synthetic resins to be added include epoxy resin, phenolic resin, melamine resin and unsaturated polyester resin.

The form of the resin-molded article may be any of fiber, nonwoven fabric, film and sheet. The resin composition may be impregnated into an inorganic or organic reinforcing material in the form of fiber, nonwoven fabric or woven fabric and thereafter cured and molded to obtain the resin-molded article.

Laminating such resin-molded article with a substrate can form a laminated sheet. Practical examples of the substrate include woven fabric and nonwoven fabric each composed of inorganic fibers such as glass, organic fibers such as polyester, aramid, polyamide, polyacrylate or polyimide and natural fibers such as cotton and also include papers, etc. It is possible to integrate the resin composition with the substrate by applying the resin composition over the substrate or immersing the substrate in the resin composition.

The amount of the resin composition to be used is preferably 30 to 80 parts by mass expressed in terms of solid content in the resin composition in parts by mass per 100 parts by mass totalizing said solid content and the substrate. In this case, solid content in the resin composition consists of the resin bearing at least two reactive functional groups reactive with a carboxylic group, phosphorus-containing carboxylic acid derivative and the curing agent to be blended on demand. The amount thereof to be used, when being less than 30 parts by mass, sometimes induces such defect as uneven distribution of the solid content amount to be impregnated into the substrate, thereby deteriorating the heat resistance of the objective laminated sheet and causing fluctuation of the electrical characteristics. On the contrary, the amount thereof to be used, when being more than 80 parts by mass, sometimes brings about unreasonably large variation of the thickness of the objective laminated sheet.

Thereafter a prepreg is obtained by curing the resin composition by means of heating, light irradiation or combination of heating and light irradiation. In the case where the resin composition contains a solvent, the solvent may be removed prior to curing the resin. The objective laminated sheet is obtained by superimposing a plurality of the prepregs obtained in such a manner, locating as necessary, metal foils over either a surface or both surfaces thereof and then heat treating the prepregs. It is possible in the case of forming the laminated sheet to combine the above-mentioned prepreg and a prepreg in which a resin composition other than that of the present invention has been impregnated into a substrate.

A covered product is obtainable which has a covering layer or layers over either a surface or both surfaces of any of various substrates by applying the resin composition according to the present invention over the surface/s. The covered product is used usually after curing, but may be used in a state of uncuring. Examples of the use in an uncured state include a seal tape which is formed by covering the resin composition over a sheet so that the covered surface constitutes a tacky adhesive surface. Examples of the covered products (coated articles) include electronic products, structures, wooden products, metallic products, plastics products, rubber products, processed paper, ceramics products and glass products and more specifically, electronic products, automobiles, metallic sheet such as steel sheets, two-wheeled vehicles, marine vessels and ships, railway rolling stocks, airplanes, furniture, musical instruments, electrical appliances, building materials, containers, office supplies, sporting goods and toys.

Coating methods for the resin composition according to the present invention is exemplified by conventionally used methods such as brush coating, spray coating, immersion coating, flow coating and the like.

Further, a resin cast material is obtainable by casting the resin composition into a casting mold and then curing the same. A general casting method is exemplified by vacuum casting method, namely a method which comprises sufficiently uniformly heating and mixing in advance, the resin composition, mixing the composition by means of an agitator or the like, vacuum casting the composition and curing the same by heating or the like to obtain a cast product. The cast material thus obtained, when applied to covering or insulation for an electronic part or electrical part, is made into a resin product imparted with flame retardancy.

In addition, the resin composition according to the present invention is usable as a resin sealing material for an electronic part and the like. In this case, the resin sealing material is usable in the form of liquid, or by tablet having a dimension and mass matching with molding conditions. As a method in which epoxy resin is used as the resin sealing material for sealing a device, a low-pressure transfer molding method is most common, but injection molding method and compression molding method may also be used.

Examples of electronic parts obtainable by sealing a device with the resin sealing material include a device which is mounted to a carrying member and necessary portion of which is sealed with epoxy resin, wherein the carrying member is exemplified by lead frame, already wired tape carriers, wiring boards, glass, silicon, wafer and the like, and the device is exemplified by active elements such as a semiconductor chip, transistor, diode and thruster; passive elements such as a capacitor, resistor and coil; a light-emitting diode (LED) and the like.

Further, examples of the electronic parts include general resin-sealed type IC, which is produced by fixing a semi-conductor device on a lead frame, connecting a terminal part of an element such as a bonding pad to a lead part by wire bonding or bump and thereafter, sealing the connection by transfer molding or the like by the use of an epoxy resin molded article for sealing; such as DIP (Dual Inline Packing), PLCC (Plastic Leaded Chip Carrier), QFP (Quad Flat Package), SOP (Small Outline Package), SOJ (Small Outline J-lead Package), TQFP (Thin Quad Flat Package), etc.; TCP (Tape Carrier Package) in which a semiconductor that is connected to a tape carrier by bump is sealed with the epoxy resin molded article for sealing; COB (Chip On Board) Module which is produced by sealing, with the epoxy resin molded article for sealing, an active element such as a semiconductor chip, transistor, diode and thyristor and/or passive element such as a capacitor, resistor and coil, each being connected onto wirings formed on a wiring board or glass by means of wire bonding, flip chip bonding, soldering or the like; hybrid IC; multi-chip module; BGA (Ball Grid Array) which is produced by mounting an element to the surface of an organic substrate in which a terminal for connecting a wiring board is formed on the rear side, connecting the element to the wiring formed on the organic substrate by wire bonding or bump and thereafter sealing the device with the resin composition; and CSP (Chip Size Package). Moreover the resin composition according to the present invention is effectively usable for a printed circuit board.

In addition, a covering material, an adhesive and the like are obtained from the phosphorus-containing carboxylic acid derivative or a resin composition containing the same. The covering material and adhesive obtained therefrom can manifest excellent solubility in organic solvents, favorable flame retardancy, heat resistance and the like on the basis of the characteristics inherent in the phosphorus-containing carboxylic acid derivative according to the present invention.

As described hereinbefore, the phosphorus-containing carboxylic acid derivative according to the present invention, in which the carboxylic groups are modified (blocked) with the vinyl ether, vinyl thioether, divinyl ether or divinyl thioether, is lowered in polarity, and thereby is excellent in solubility in organic solvents, especially in non-polar organic solvents and beside, in compatibility with a variety of synthetic resins. Besides, the phosphorus-containing carboxylic acid derivative according to the present invention has favorable stability, since even when being mixed with a resin bearing a group reactive with a carboxylic acid, curing reaction based on the carboxylic group does not proceed.

Moreover, the above-mentioned phosphorus-containing carboxylic acid derivative, which contains phosphorus atom as an essential component, is excellent in self-fire-extinguishing properties and flame retardancy. Further, the foregoing phosphorus-containing carboxylic acid derivative, which is endowed with antioxidant action, is excellent in coloring prevention and besides, can exhibit excellent heat resistance, since it has such properties as absorbing excess energy locally applied by heat, or light.

Furthermore, the phosphorus-containing carboxylic acid derivative according to the present invention is easily producible in high yield by allowing the phosphorus-containing carboxylic acid bearing both a carboxylic group and phosphorus atoms to react with a vinyl ether compound or vinyl thioether compound.

The above-mentioned resin composition is obtained from the phosphorus-containing carboxylic acid derivative according to the present invention and the synthetic resin bearing in its molecule, at least two reactive functional groups reactive with a carboxylic group, and is capable of exerting the characteristics inherent in the aforesaid derivative. Likewise, a resin-molded article formed by curing the resin composition is also capable of exerting the characteristics inherent in the aforesaid resin.

In what follows, the embodiments of the present invention will be described in more detail with reference to working examples, which however shall never limit the present invention thereto insofar as it does not depart form the spirit and purport thereof.

In the following, the compounds to be used in the present invention will be described.

(a) 9,10-dihydro-9-oxa-10-phosphaphenanthrene-10-oxide, the compound represented by the foregoing formula (16) {available from Sanko Co., Ltd. under the trade name "SANKO-HCA"}, hereinafter abbreviated to "HCA".

(b) M-Acid {available from Sanko Co., Ltd.}, common name, which will be also used as such in this specification, the compound represented by above-mentioned formula (15).

(c) diethylhydrogen phosphite (hereinafter abbreviated to "DEHP"), the compound represented by the following formula (c):

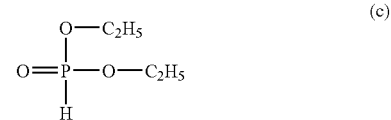

(d) diphenylhydrogen phosphite (hereinafter abbreviated to "DPHP"), the compound represented by the following formula (d):

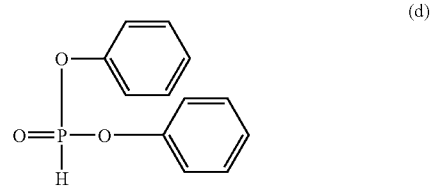

(e) 2-phosphonobutane-1,2,4-tricarboxylic acid (hereinafter abbreviated to "PBTC", available from Jouhoku Chemical Industrial Co., Ltd.), the compound represented by the following formula (e):

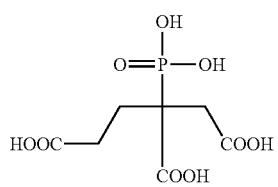

(e)

In the following, explanations will be described about the measuring method and evaluation method used in the working examples of the present invention.

1. Measuring Conditions for $^1$H-NMR
   Type of instrument: 400 MHz type "Advance 400", produced by Japan Bulcar Co., Ltd.
   Number of times of integration: 16 times
   Solvent: $CD_3OD$, TMS standard in Reference Examples 1 to 7 and in Comparative Reference Example 1 and $CDCl_3$, TMS standard in Examples 1 to 10.

2. Measurement of Acid Equivalent
   The acid equivalent was measured in accordance with JIS K 0070-3 (1992).

3. Measurement of Yield and Purity
   The yield and purity were determined by liquid chromatography (hereinafter abbreviated to "LC"), followed by conversion.
   Measuring Conditions for LC
   Type of instrument: "SC-8010" produced by Tosoh Corporation.
   Column: "Inertsil ODS-3" produced by GL Science Co., Ltd.
   Elute: mixed liquid of methanol/propionic acid (4/1)

4. Measuring Conditions for IR
   Type of instrument: "FT/IR-600" produced by Japan Spectroscopy Co., Ltd.
   Cell: tablet method employing potassium bromide
   Resolution: 4 cm$^{-1}$
   Number of times of integration: 16 times 5. Measurement of Molecular Weight
   The molecular weight was calculated from gel size permeation chromatography (hereinafter abbreviated to "GPC")
   Type of instrument: "SC-8010" produced by Tosoh Corporation.
   Column: "SHODEX K-801" produced by Showa Denko Co., Ltd.
   Elute: tetrahydrofuran (THF)
   Detector: RI 6. Solubility Test
   One part by weight of each of samples and 4 parts by weight of each of solvents were placed into a vial, and the resultant mixture was stirred at room temperature for one hour with the use a rotor. After the stirring, the solubility of the sample was visually observed.

7. Storage Stability Test
   One part by weight of each of samples and one part by weight of epoxy resin of phenol/novolak type ("YDPN 638", trade name; available from Toto Kasei Co., Ltd.) were placed into a vial and the resultant mixture was stirred at room temperature for one hour with the use of a rotor, and after the stirring, it was allowed to stand at room temperature for 30 days. Then a visual observation was made about an increase in the viscosity thereof.

8. Combustion Test
   The combustion test was carried out in accordance with UL (Underwriter Laboratories) 94 Thin Material Vertical Burning Test.

9. Measurement of Acid Value
   The acid value was calculated by accurately weighing a sample, and by titration with potassium hydroxide/ethanol solution having a known concentration.

10. Solvent Resistance Test
    Solvent resistance was tested by rubbing a sample in 30 reciprocation times with kim wipe (trade name; available from Kresia Co., Ltd.) impregnated with acetone, and visually observing scratch.

11. Observation of Coloring
    A sample film was heated in a hot air wind oven under the heating conditions of 230° C. for 30 minutes, and the extent of coloring was visually observed.

12. Heat Resistance Test
    A sample film was heated, and the temperature at which the weight thereof was decreased by 5% was regarded as thermal decomposition temperature. The heat resistance was evaluated by the standard whether the thermal decomposition temperature is at least 330° C. or not.

REFERENCE EXAMPLE 1

Synthesis of M-Acid by the Use of Acetonirile as the Solvent

A four-neck flask equipped with a reflux condenser, a stirrer and a thermometer was charged with 30.1 parts by weight of HCA, 19.9 parts by weight of itaconic acid and 50.0 parts by weight of acetonitrile, and the resultant mixture was reacted with one another at 81° C. for 4 hours under stirring. When the reaction liquid thus formed was cooled to room temperature, white crystal was precipitated and accordingly separated by filtration. When the white crystal thus obtained was dried with the use of a vacuum dryer under the conditions of 20 mmHg, 80° C. for one hour, there was obtained 44.7 g of a white crystal having a melting point in the range of 191 to 198° C. and an acid value of 171 g/mol. A measurement was made of $^1$H-NMR of the product with a result that peaks were confirmed at 7.27 to 8.15 ppm (m, H8), at 3.31 to 3.32 ppm (m, H1) and at 2.50 to 2.82 ppm (m, H2), and thus the structure of product represented by the foregoing formula (15) was confirmed.

Further, a measurement was made of the purity of the product. As a result, the purity was 98.4% by weight, while containing 1.6% by weight of itaconic acid as an impurity. The yield thereof calculated on the basis of the amount of charge was 88.0% by weight.

REFERENCE EXAMPLE 2

Synthesis of M-Acid by the Use of Acetonirile and PMAc as the Solvents

A four-neck flask equipped with a reflux condenser, a stirrer and a thermometer was charged with 30.1 parts by weight of HCA, 19.9 parts by weight of itaconic acid, 20.0 parts by weight of acetonitrile and 30.0 parts by weight of PMAc (methoxypropyl acetate), and the resultant mixture was reacted with one another at 110° C. for 4 hours under stirring. When the reaction liquid thus formed was cooled to room temperature, white crystal was precipitated and accordingly separated by filtration. When the white crystal thus obtained was dried with the use of a vacuum dryer under the conditions of 20 mmHg, 80° C. for one hour, there was obtained 46.6 g of a white crystal having a melting point in the range of 196 to 198° C. and an acid value of 172 g/mol. A measurement was made of $^1$H-NMR of the product with a result that peaks were confirmed at 7.27 to 8.15 ppm (m, H8), at 3.31 to 3.32 ppm (m, H1) and at 2.50 to 2.82 ppm (m, H2), and thus the structure of product represented by the foregoing formula (15) was confirmed.

Further, a measurement was made of the purity of the product. As a result, the purity was 99.4% by weight, while containing 0.6% by weight of itaconic acid as an impurity. The yield thereof calculated on the basis of the amount of charge was 92.6% by weight.

REFERENCE EXAMPLE 3

Synthesis of M-Acid by the Use of PMAc as the Solvents

A four-neck flask equipped with a reflux condenser, a stirrer and a thermometer was charged with 30.1 parts by weight of HCA, 19.9 parts by weight of itaconic acid and 30.0 parts by weight of PMAc (methoxypropyl acetate), and the resultant mixture was reacted with one another at 122° C. for 2 hours under stirring. At that time, white crystal was precipitated. Further stirring was continued for one hour, the reaction liquid thus formed was cooled to room temperature, and the white crystal was separated by filtration. The white crystal thus obtained in an amount of 20 parts by weight was dried with the use of a vacuum dryer under the conditions of 20 mmHg, 80° C. for one hour, there was obtained 48.4 g of a white crystal having a melting point in the range of 196 to 198° C. and an acid value of 172 g/mol. A measurement was made of $^1$H-NMR of the product with a result that peaks were confirmed at 7.27 to 8.15 ppm (m, H8), at 3.31 to 3.32 ppm (m, H1) and at 2.50 to 2.82 ppm (m, H2), and thus the structure of product represented by the foregoing formula (15) was confirmed.

Further, a measurement was made of the purity of the product. As a result, the purity was 99.6% by weight, while containing 0.2% by weight of itaconic acid as an impurity. The yield thereof calculated on the basis of the amount of charge was 96.4% by weight.

REFERENCE EXAMPLE 4

Synthesis of M-Acid by the Use of Acetonitrile as the Solvent and DBU as the Catalyst A four-neck flask equipped with a reflux condenser, a stirrer and a thermometer was charged with 30.1 parts by weight of HCA, 19.9 parts by weight of itaconic acid, 50.0 parts by weight of acetonitrile and 0.5 part by weight of DBU, and the resultant mixture was reacted with one another at 81° C. for 4 hours under stirring. When the reaction liquid thus formed was cooled to room temperature, white crystal was precipitated and accordingly separated by filtration. When the white crystal thus obtained was dried with the use of a vacuum dryer under the conditions of 20 mmHg, 80° C. for one hour, there was obtained 47.4 g of a white crystal having a melting point in the range of 193 to 198° C. and an acid value of 170 g/mol. A measurement was made of $^1$H-NMR of the product with a result that peaks were confirmed at 7.27 to 8.15 ppm (m, H8), at 3.31 to 3.32 ppm (m, H1) and at 2.50 to 2.82 ppm (m, H2), and thus the structure of product represented by the foregoing formula (15) was confirmed.

Further, a measurement was made of the purity of the product. As a result, the purity was 98.7% by weight, while containing 1.2% by weight of itaconic acid as an impurity. The yield thereof calculated on the basis of the amount of charge was 93.6% by weight.

REFERENCE EXAMPLE 5

Synthesis of Adduct of DEHP with Itaconic Acid by the Use of PMAc as the Solvent A four-neck flask equipped with a reflux condenser, a stirrer and a thermometer was charged with 36.0 parts by weight of DEHP, 34.0 parts by weight of itaconic acid and 30.0 parts by weight of PMAc (methoxypropyl acetate), and the resultant mixture was reacted with one another at 120° C. for 6 hours under stirring. When the PMAc was distilled away under reduced pressure (20 mmHg) at the temperature of 80° C. for one hour, 70.3 parts by weight of yellow liquid was obtained. A measurement was made of $^1$H-NMR of the product with a result that peaks were confirmed at 4.05 to 4.20 ppm (m, H6), at 3.30 to 3.35 ppm (m, H2), at 2.06 to 2.12 ppm (m, H1) and 1.17 to 1.34 (m, H6), and thus, it was confirmed that the structure of the product was represented by the following formula (f):

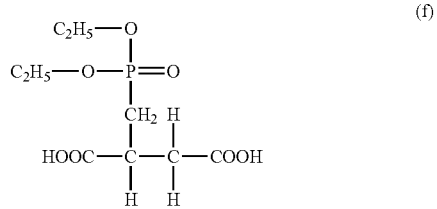

Further, a measurement was made of the purity of the product. As a result, the purity was 97.6% by weight, while containing PMAc, DEHP and itaconic acid each as trace impurity. The yield thereof calculated on the basis of the amount of charge was 98.0% by weight. Hereinafter, the resultant phosphorus-containing carboxylic acid compound is referred to as DEHP-Ita A.

REFERENCE EXAMPLE 6

Synthesis of Adduct of DEHP with Maleic Acid by the Use of Acetonitrile as the Solvent A four-neck flask equipped with a reflux condenser, a stirrer and a thermometer was charged with 38.0 parts by weight of DEHP, 32.0 parts by weight of maleic acid and 30.0 parts by weight of acetonitrile, and the resultant mixture was reacted with one another in an autoclave at 110° C. for 4 hours under stirring. When the PMAc was distilled away under reduced pressure (20 mmHg) at the temperature of 100° C. for one hour, 69.4 parts by weight of yellow liquid was obtained. A measurement was made of $^1$H-NMR of the product with a result that peaks were confirmed at 4.12 to 4.22 ppm (m, H4), at 3.28 to 3.31 ppm (m, H2), at 2.06 to 2.18 ppm (m, H1) and 1.10 to 1.36 (m, H6), and thus, it was confirmed that the structure of the product was represented by the following formula (g):

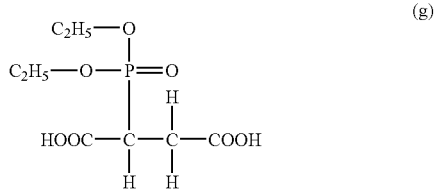

Further, a measurement was made of the purity of the product. As a result, the purity was 96.5% by weight, while containing PMAc, DEHP and itaconic acid each as trace impurity. The yield thereof calculated on the basis of the amount of charge was 69.7% by weight.

Hereinafter, the resultant phosphorus-containing carboxylic acid compound is referred to as DEHP-Mal A.

REFERENCE EXAMPLE 7

Synthesis of Adduct of DPHP with Itaconic Acid by the Use of PMAc as the Solvent A four-neck flask equipped with a reflux condenser, a stirrer and a thermometer was charged with 45.0 parts by weight of DPHE, 25.0 parts by weight of itaconic acid and 30.0 parts by weight of PMAc (methoxypropyl acetate), and the resultant mixture was reacted with one another at 120° C. for 6 hours under stirring. When the PMAc was distilled away under reduced pressure (20 mmHg) at the temperature of 100° C. for one hour, 69.5 parts by weight of yellow liquid was obtained. A measurement was made of $^1$H-NMR of the product with a result that peaks were confirmed at 7.15 to 7.65 ppm (m, H10), at 4.00 to 4.09 ppm (m, H2), at 3.32 to 3.33 ppm (m, H1) and at 2.04 to 2.05 (m, H2), and thus, it was confirmed that the structure of the product was represented by the following formula (h):

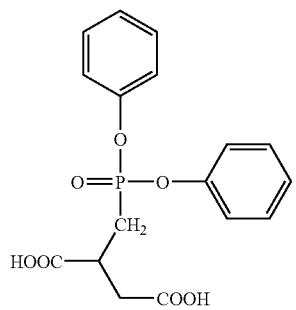

(h)

Further, a measurement was made of the purity of the product. As a result, the purity was 98.5% by weight, while containing PMAc, DEHP and itaconic acid each as trace impurity. The yield thereof calculated on the basis of the amount of charge was 97.8% by weight.

Hereinafter, the resultant phosphorus-containing carboxylic acid compound is referred to as DPHP-Ita A.

COMPARATIVE REFERENCE EXAMPLE 1

Synthesis of M-Acid by the Use of Propionic Acid as the Solvent

A four-neck flask equipped with a reflux condenser, a stirrer and a thermometer was charged with 30.1 parts by weight of HCA, 19.9 parts by weight of itaconic acid and 50.0 parts by weight of propionic acid, and the resultant mixture was reacted with one another at 140° C. for 8 hours under stirring. During the course of the reaction, temperature control was difficult because of vigorous refluxing. When the reaction liquid thus formed was cooled to room temperature under stirring for 12 hours, white crystal was precipitated and accordingly separated by filtration. The white crystal thus obtained was dried with the use of a vacuum dryer under the conditions of 20 mmHg, 80° C. for one hour, but removal of propionic acid odor was impossible. As a result, there was obtained 46.5 g of a white crystal having a melting point in the range of 193 to 196° C. and an acid value of 167 g/mol. A measurement was made of $^1$H-NMR of the product with a result that peaks were confirmed at 7.27 to 8.15 ppm (m, H8), at 3.31 to 3.32 ppm (m, H1) and at 2.50 to 2.82 ppm (m, H2), and thus the structure of product represented by the foregoing formula (15) was confirmed.

Further, a measurement was made of the purity of the product. As a result, the purity was 98.7% by weight, while containing 0.5% by weight of itaconic acid and 0.4% by weight of propionic acid each as an impurity. The yield thereof calculated on the basis of the amount of charge was 95.2% by weight.

The white crystal thus obtained had strong odor originating from propionic acid. In view of the above, 10 parts by weight of the white crystal was suspended in 100 parts by weight of water, and the resultant suspension was filtered. The operation of washing with 100 parts by weight of water was repeated 5 times, but removal of irritating odor of propionic acid remained impossible.

COMPARATIVE REFERENCE EXAMPLE 2

Synthesis of M-Acid by the Use of Water as the Solvent

A four-neck flask equipped with a reflux condenser, a stirrer and a thermometer was charged with 30.1 parts by weight of HCA, 19.9 parts by weight of itaconic acid and 50.0 parts by weight of water, and the resultant mixture was stirred at 100° C. for one hour. During the stirring, the solution turned into powder without proceeding of any reaction.

COMPARATIVE REFERENCE EXAMPLE 3

Synthesis of M-Acid by the Use of Isopropanol as the Solvent

A four-neck flask equipped with a reflux condenser, a stirrer and a thermometer was charged with 30.1 parts by weight of HCA, 19.9 parts by weight of itaconic acid and 50.0 parts by weight of isopropanol, and the resultant mixture was reacted at 140° C. for 8 hours under stirring. After the completion of the reaction, the reaction liquid thus formed was cooled to room temperature, while stirring for 12 hours, but no solid was precipitated. Then, the reaction liquid was analyzed, but no M-Acid was detected.

COMPARATIVE REFERENCE EXAMPLE 4

Synthesis of M-Acid by the Use of Methyl Isobutyl Ketone as the Solvent

A four-neck flask equipped with a reflux condenser, a stirrer and a thermometer was charged with 30.1 parts by weight of HCA, 19.9 parts by weight of itaconic acid and 50.0 parts by weight of methyl isobutyl ketone, and the resultant mixture was reacted at 140° C. for 8 hours under stirring. After the completion of the reaction, the reaction liquid thus formed was cooled to room temperature, while stirring for 12 hours, but no solid was precipitated. Then, the reaction liquid was analyzed, but no M-Acid was detected.

COMPARATIVE REFERENCE EXAMPLE 5

Synthesis of M-Acid by the Use of Cyclohexanone as the Solvent

A four-neck flask equipped with a reflux condenser, a stirrer and a thermometer was charged with 30.1 parts by weight of HCA, 19.9 parts by weight of itaconic acid and 50.0 parts by weight of cyclohexanone, and the resultant mixture was reacted at 140° C. for 8 hours under stirring. After the completion of the reaction, the reaction liquid thus formed was cooled to room temperature, while stirring for 12 hours, but no solid was precipitated. Then, the reaction liquid was analyzed, but no M-Acid was detected.

COMPARATIVE REFERENCE EXAMPLE 6

Synthesis of M-Acid by the Use of Xylene as the Solvent

A four-neck flask equipped with a reflux condenser, a stirrer and a thermometer was charged with 30.1 parts by weight of HCA, 19.9 parts by weight of itaconic acid and 50.0 parts by weight of xylene, and the resultant mixture was reacted at 140° C. for 8 hours under stirring. After the completion of the reaction, the reaction liquid thus formed was cooled to room temperature, while stirring for 12 hours, but no solid was precipitated. Then, the reaction liquid was analyzed, but no M-Acid was detected.

EXAMPLE 1

Phosphorus-Containing Carboxylic Acid Derivative Produced by Modifying M-Acid with N-Propylvinyl Ether)

A four-neck flask equipped with a reflux condenser, a stirrer and a thermometer was charged with 53.4 parts by weight of M-Acid which had been obtained in the Reference Example 3, 31.9 parts by weight of n-propylvinyl ether, 14.7 parts by weight of 2-butanone and 0.05 part by weight of AP-8 (phosphoric acid catalyst, available from by Daihachi Chemical Industrial Co., Ltd.). The resultant mixture was stirred under the conditions of 85° C. for 3 hours. The reactivity which was calculated from the measured acid value was 99.3%. Then unreacted n-propylvinyl ether and unreacted 2-butanone were removed with the use of an evaporator under the conditions of 20 mmHg and 50° C. (the acid value after the vacuum concentration being 8.32 mg KOH/g).

Figure 2:
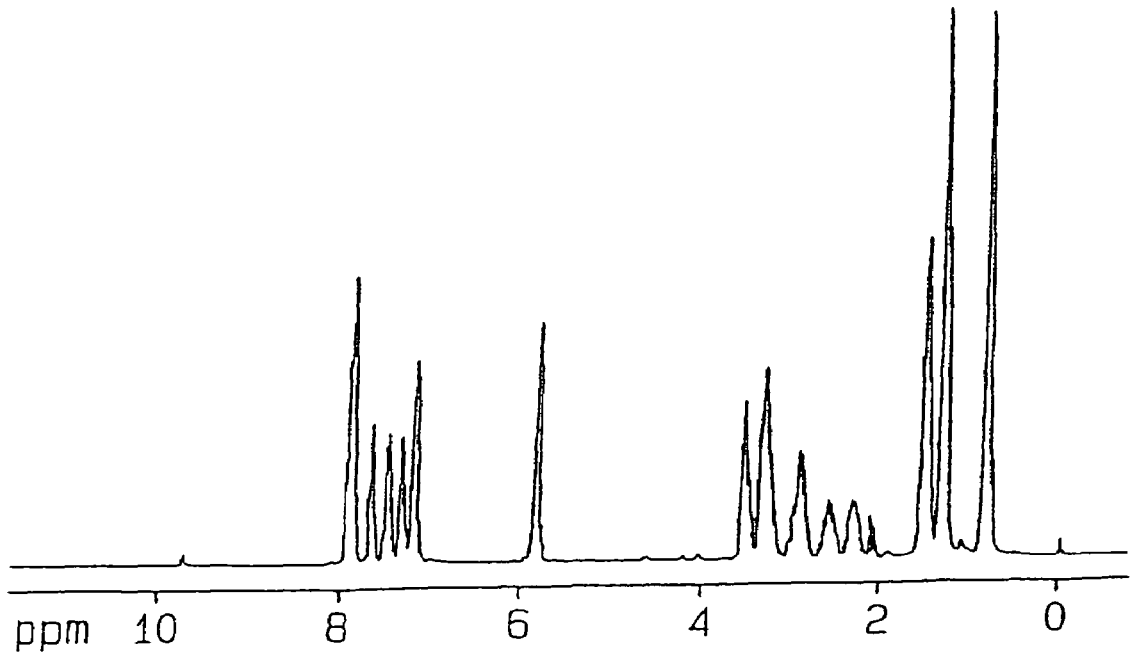
FIG. 2 is a nuclear magnetic resonance spectrum of the product obtained in Example 1.

The product thus obtained was colorless transparent highly viscous liquid. The infrared absorption spectrum thereof is shown as FIG. 1, and the $^1$H-NMR spectrum thereof is shown as FIG. 2.

The facts that the acid value of the product was remarkably low as compared with that of the M-acid, and that any absorption assigned to the carboxylic group was not confirmed from the infrared absorption spectrum have rendered it possible to confirm that the carboxylic group of the M-acid was modified with the n-propylvinyl ether. That is to say, the objective phosphorus-containing carboxylic acid derivative has the structure represented by the following formula (i):

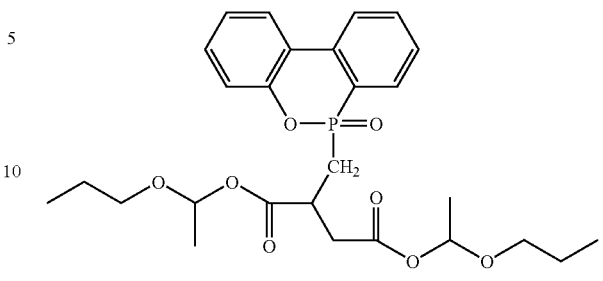

(i)

The objective phosphorus-containing carboxylic acid derivative had in its one molecule, two functional groups represented by the foregoing formula (2) and had phosphorus atom content of 5.98% by weight. In the following, the phosphorus-containing carboxylic acid derivative thus obtained is referred to as Block acid A. The solubility test and the storage stability test were carried out for the Block acid A. The results are shown in Table 1.

EXAMPLE 2

Figure 3:
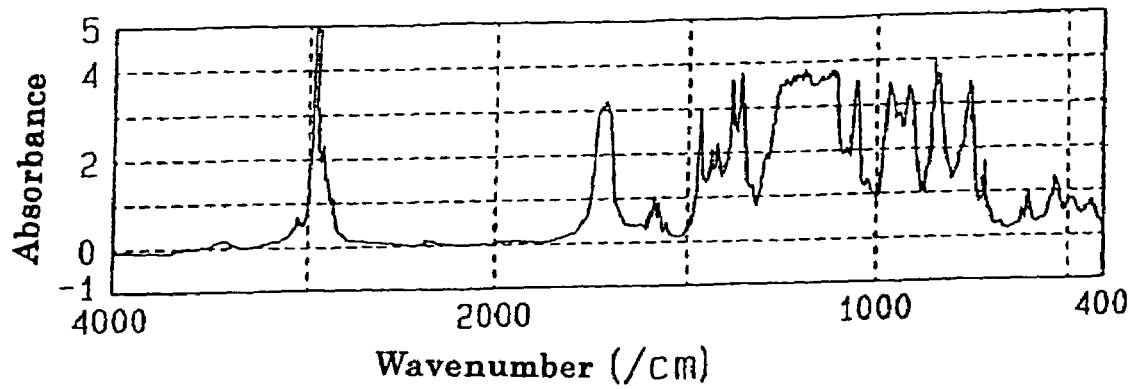
FIG. 3 is an infrared absorption spectrum of the product obtained in Example 2.

Phosphorus-Containing Carboxylic Acid Derivative Produced by Modifying M-Acid with Tert-Butylvinyl Ether A four-neck flask equipped with a reflux condenser, a stirrer and a thermometer was charged with 25.4 parts by weight of M-Acid which had been obtained in the foregoing Reference Example 3, 17.6 parts by weight of tert-butylvinyl ether, 7.1 parts by weight of 2-butanone and 0.025 part by weight of AP-8 (phosphoric acid catalyst, available from Daihachi Chemical Industrial Co., Ltd.). The resultant mixture was stirred under the conditions of 85° C. for 2 hours. The reactivity which was calculated from the measured acid value was 99.1%. Then unreacted tert-butylvinyl ether and unreacted 2-butanone were removed with the use of an evaporator under the conditions of 20 mmHg and 50° C. (the acid value after the vacuum concentration being 9.61 mg KOH/g). The product thus obtained was light yellow transparent highly viscous liquid. The infrared absorption spectrum thereof is shown as FIG. 3. The facts that the acid value of the product was remarkably low as compared with that of the M-acid, and that any absorption assigned to the carboxylic group was not confirmed from the infrared absorption spectrum have rendered it possible to confirm that the carboxylic group of the M-Acid was modified with the tert-butylvinyl ether. That is to say, the objective phosphorus-containing carboxylic acid derivative has the structure represented by the following formula (j):

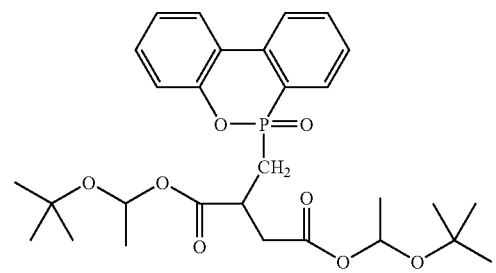

(j)

The objective phosphorus-containing carboxylic acid derivative had in its one molecule, two functional groups represented by the foregoing formula (2) and had phosphorus atom content of 5.67% by weight.

In the following, the phosphorus-containing carboxylic acid derivative thus obtained is referred to as Block acid B. In the same manner as in Example 1, the solubility test and the storage stability test were carried out for the Block acid B. The results are shown in Table 1.

EXAMPLE 3

Phosphorus-Containing Carboxylic Acid Derivative Produced by Modifying M-Acid with Ethylhexylvinyl Ether A four-neck flask equipped with a reflux condenser, a stirrer and a thermometer was charged with 21.0 parts by weight of M-Acid which had been obtained in the foregoing Reference Example 3, 22.8 parts by weight of ethylhexylvinyl ether, 6.2 parts by weight of 2-butanone and 0.025 part by weight of AP-8 (phosphoric acid catalyst, available from Daihachi Chemical Industrial Co., Ltd.). The resultant mixture was stirred under the conditions of 120° C. for 2 hours. The reactivity which was calculated from the measured acid value was 99.6%. Then unreacted ethylhexylvinyl ether and unreacted 2-butanone were removed with the use of an evaporator under the conditions of 20 mmHg and 50° C. (the acid value after the vacuum concentration being 4.47 mg KOH/g.)

Figure 4:
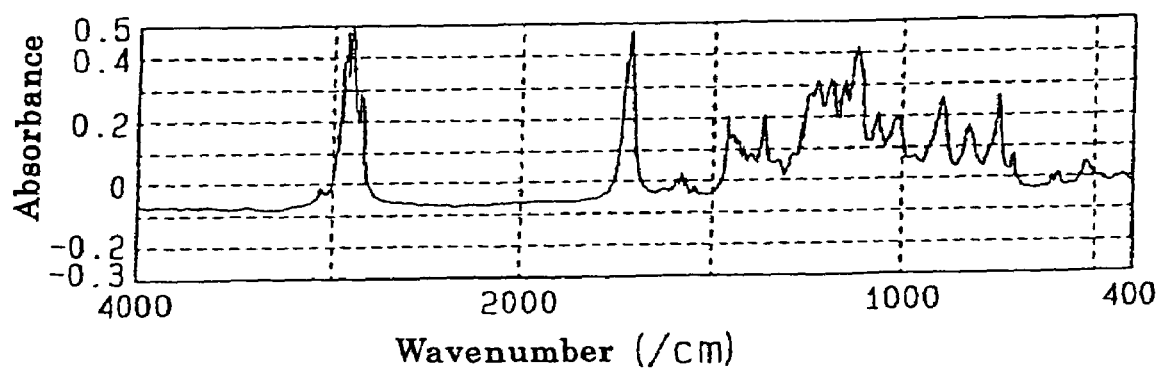
FIG. 4 is an infrared absorption spectrum of the product obtained in Example 3.

The product thus obtained was light yellow transparent highly viscous liquid. The infrared absorption spectrum thereof is shown as FIG. 4. The facts that the acid value of the product was remarkably low as compared with that of the M-Acid, and that any absorption assigned to the carboxylic group was not confirmed from the infrared absorption spectrum have rendered it possible to confirm that the carboxylic group of the M-Acid was modified with the ethylhexylvinyl ether. That is to say, the objective phosphorus-containing carboxylic acid derivative has the structure represented by the following formula (k):

The objective phosphorus-containing carboxylic acid derivative had in its one molecule, two functional groups represented by the foregoing formula (2) and had phosphorus atom content of 4.71% by weight.

In the following, the phosphorus-containing carboxylic acid derivative thus obtained is referred to as Block acid C. In the same manner as in Example 1, the solubility test and the storage stability test were carried out for the Block acid C. The results are shown in Table 1.

EXAMPLE 4

Figure 5:
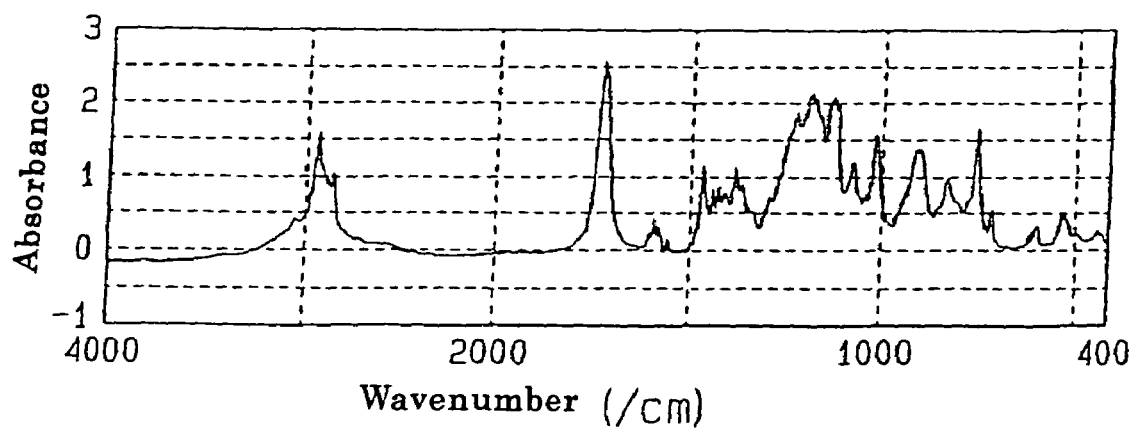
FIG. 5 is an infrared absorption spectrum of the product obtained in Example 4.

Phosphorus-Containing Carboxylic Acid Derivative Produced by Modifying M-Acid with Isobutylvinyl Ether A four-neck flask equipped with a reflux condenser, a stirrer and a thermometer was charged with 25.4 parts by weight of M-acid which had been obtained in the foregoing Reference Example 3, 17.6 parts by weight of isobutylvinyl ether, 7.1 parts by weight of 2-butanone and 0.025 part by weight of AP-8 (phosphoric acid catalyst, available from Daihachi Chemical Industrial Co., Ltd.). The resultant mixture was stirred under the conditions of 100° C. for 4 hours. The reactivity which was calculated from the measured acid value was 99.1%. Then unreacted isobutylvinyl ether and unreacted 2-butanone were removed with the use of an evaporator under the conditions of 20 mmHg and 50° C. (the acid value after the vacuum concentration being 6.73 mg KOH/g). The product thus obtained was reddish yellow transparent highly viscous liquid. The infrared absorption spectrum thereof is shown as FIG. 5. The facts that the acid value of the product was remarkably low as compared with that of the M-Acid, and that any absorption assigned to the carboxylic group was not confirmed from the infrared absorption spectrum have rendered it possible to confirm that the carboxylic group of the M-Acid was modified with the isobutylvinyl ether. That is to say, the objective phosphorus-containing carboxylic acid derivative has the structure represented by the following formula (1):

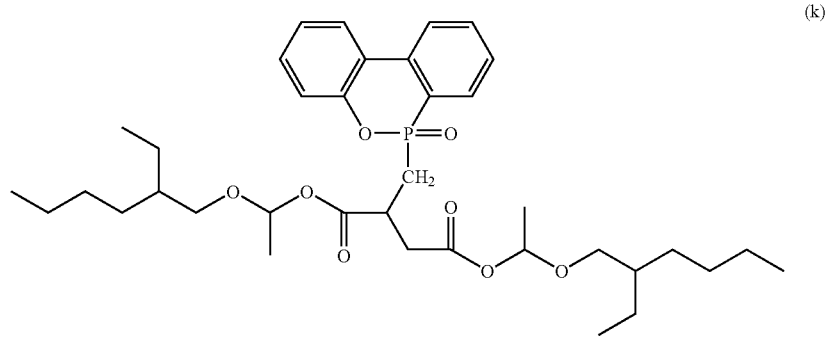

(k)

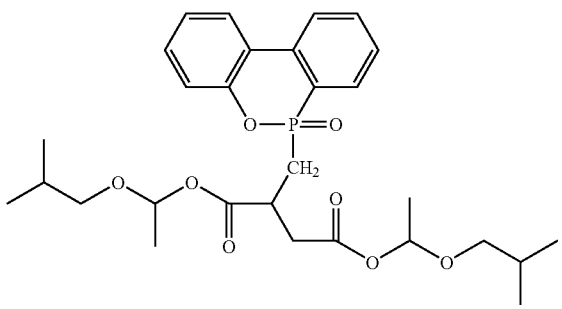

(l)

Figure 6:
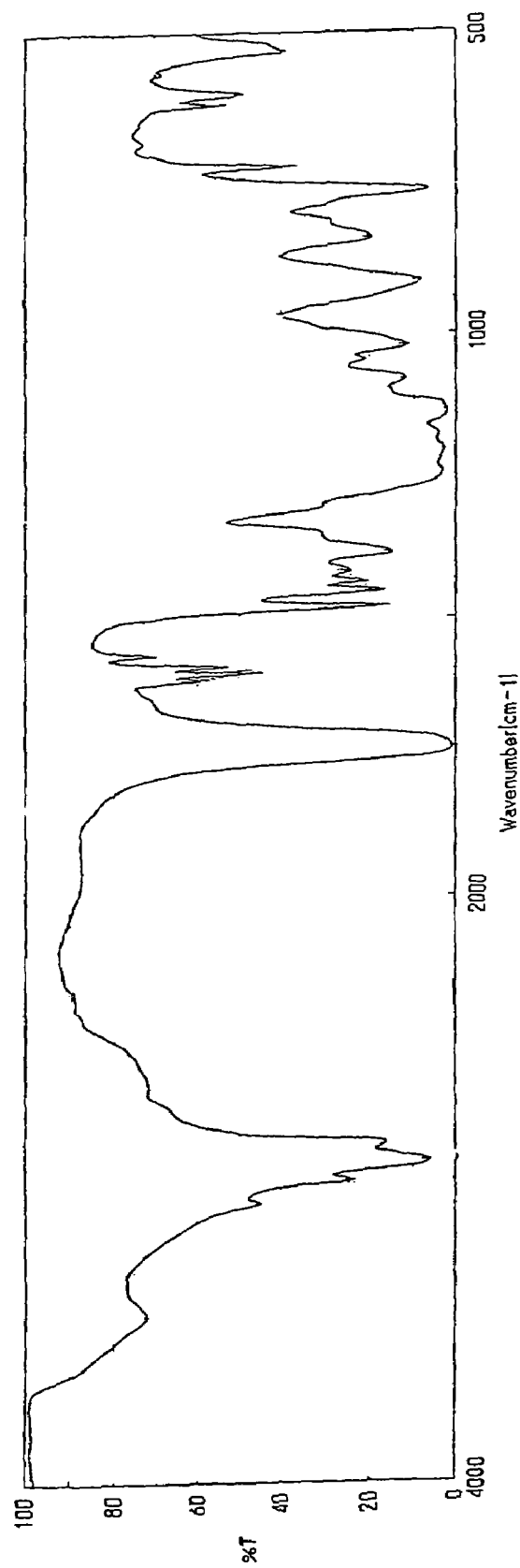
FIG. 6 is an infrared absorption spectrum of the product obtained in Example 5.
Figure 7:
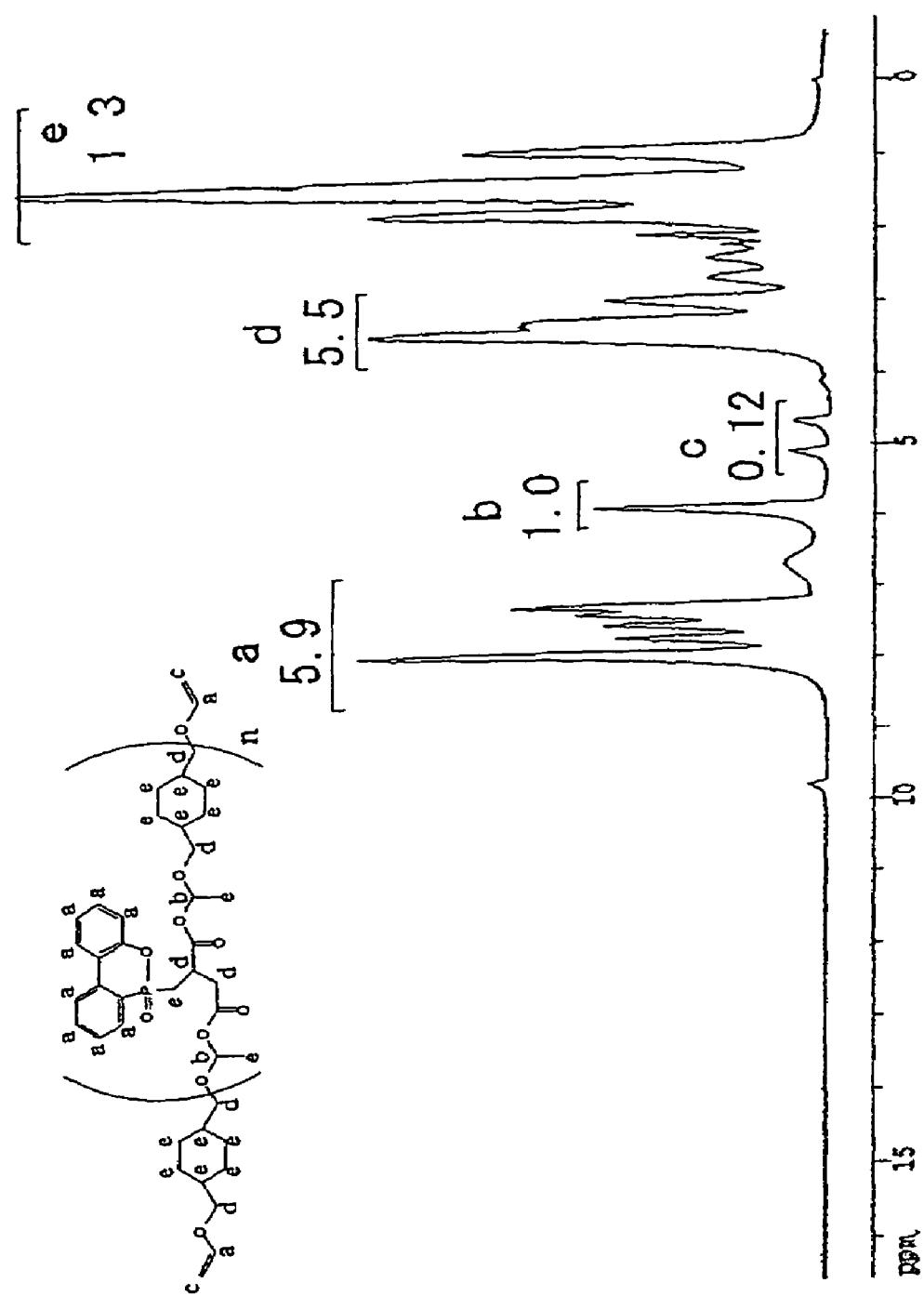
FIG. 7 is a nuclear magnetic resonance spectrum of the product obtained in Example 5.

The product thus obtained was light yellow transparent highly viscous liquid. The infrared absorption spectrum thereof is shown as FIG. 6, and the $^1$H-NMR spectrum thereof is shown as FIG. 7. Further the molecular weight thereof was measured in accordance with the foregoing GPC procedure. As a result, the weight-average molecular weight (Mw) was about 12,000, from which the average degree of polymerization "n" was calculated as being 22.

The facts that the acid value of the product was remarkably low as compared with that of the M-Acid, and that any absorption assigned to the carboxylic group was not confirmed from the infrared absorption spectrum have rendered it possible to confirm that the carboxylic group of the M-acid was modified with the CHDVE. Moreover, it can be seen from the increased molecular weight that polymerization reaction took place. That is to say, the objective phosphorus-containing carboxylic acid derivative has the structure represented by the following formula (m):

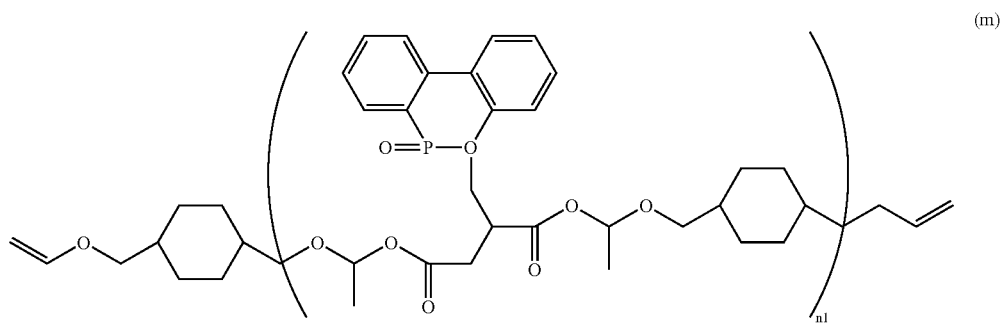

(m)

The objective phosphorus-containing carboxylic acid derivative had in its one molecule, two functional groups represented by the foregoing formula (2) and had phosphorus atom content of 4.71% by weight.

In the following, the phosphorus-containing carboxylic acid derivative thus obtained is referred to as Block acid D. In the same manner as in Example 1, the solubility test and the storage stability test were carried out for the Block acid D. The results are shown in Table 1.

EXAMPLE 5

Phosphorus-Containing Carboxylic Acid Derivative Produced by Modifying M-Acid with Cyclohexyldimethanoldivinyl Ether A four-neck flask equipped with a reflux condenser, a stirrer and a thermometer was charged with 31.3 parts by weight of M-acid which had been obtained in the foregoing Reference Example 3, 18.7 parts by weight of cyclohexyldimethanoldivinyl ether (CHDVE) and 50 parts by weight of methoxypropyl acetate (PMAc). The resultant mixture was stirred under the conditions of 100° C. for 3 hours. The reactivity which was calculated from the measured acid value was 98.3%. Then unreacted CHDVE and unreacted PMAc were removed with the use of an evaporator under the conditions of 20 mmHg and 50° C.

The objective phosphorus-containing carboxylic acid derivative had in its one molecule, 22 functional groups represented by the foregoing formula (3) and had phosphorus atom content of 5.6% by weight.

In the following, the phosphorus-containing carboxylic acid derivative thus obtained is referred to as Block acid E. In the same manner as in Example 1, the solubility test and the storage stability test were carried out for the Block acid E. The results are shown in Table 1.

EXAMPLE 6

Phosphorus-Containing Carboxylic Acid Derivative Produced by Modifying M-Acid with 1,4-Butanedioldivinyl Ether A four-neck flask equipped with a reflux condenser, a stirrer and a thermometer was charged with 34.9 parts by weight of M-Acid which had been obtained in the foregoing Reference Example 3, 15.1 parts by weight of 1,4-butanedioldivinyl ether (1,4-BDVE) and 50 parts by weight of methoxypropyl acetate (PMAc). The resultant mixture was stirred under the conditions of 100° C. for 3 hours. The reactivity which was calculated from the measured acid value was 98.6%. Then unreacted 1,4-BDVE and unreacted PMAc were removed with the use of an evaporator under the conditions of 20 mmHg and 50° C.

Figure 8:
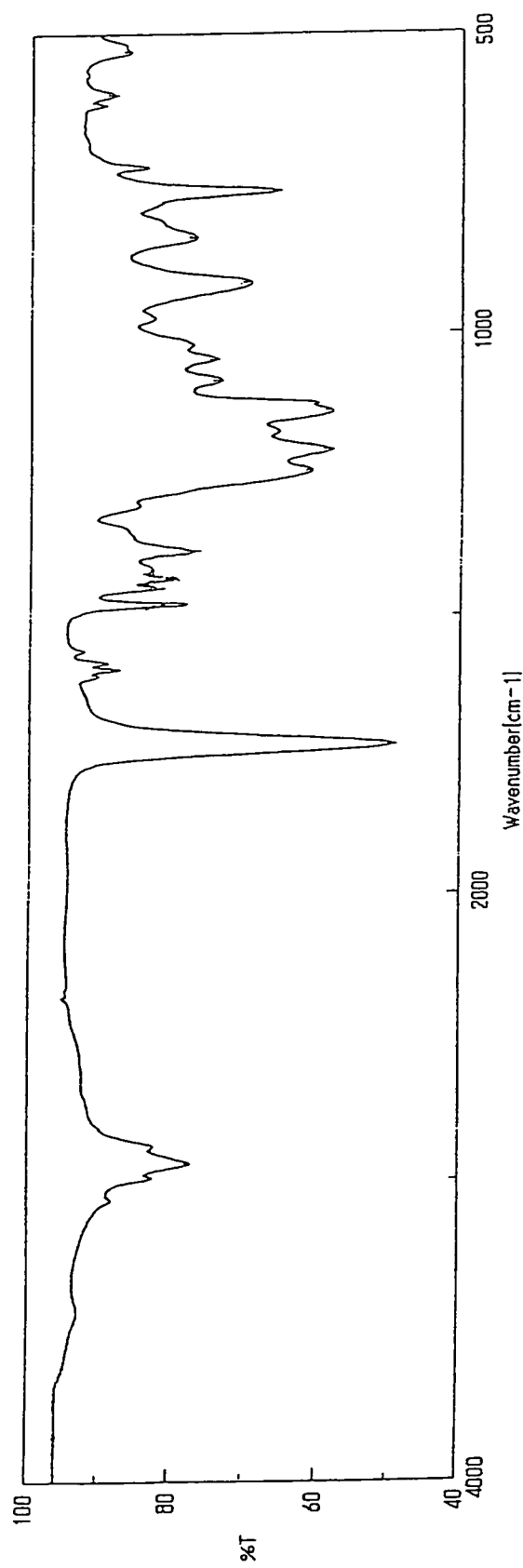
FIG. 8 is an infrared absorption of the product obtained in Example 6.
Figure 9:
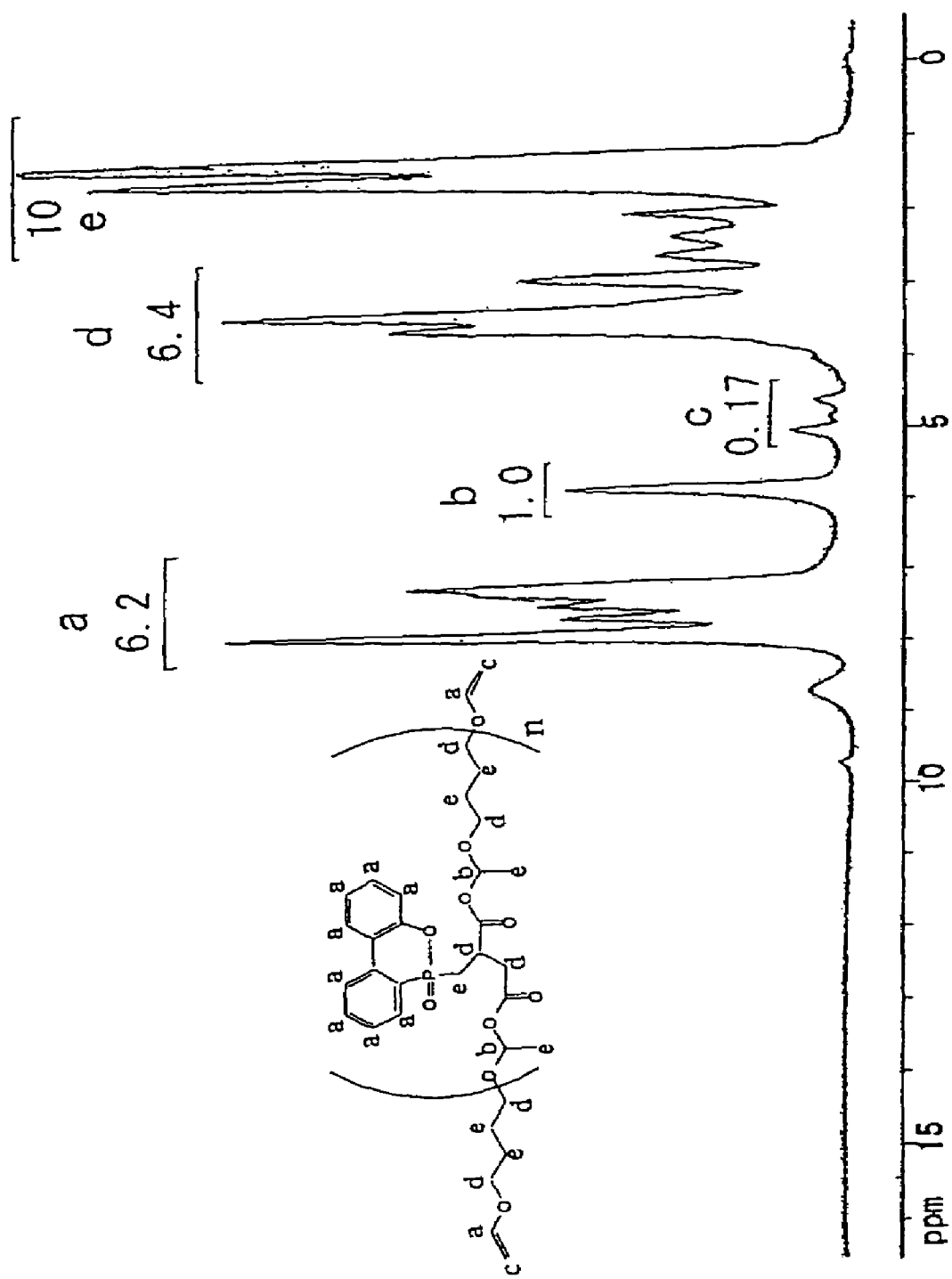
FIG. 9 is a nuclear magnetic resonance spectrum of the product obtained in Example 6.

The product thus obtained was light yellow transparent highly viscous liquid. The infrared absorption spectrum thereof is shown as FIG. 8, and the $^1$H-NMR spectrum thereof is shown as FIG. 9. Further the molecular weight thereof was measured in accordance with the foregoing GPC procedure. As a result, the weight-average molecular weight (Mw) was about 8,000, from which the average degree of polymerization "n" was calculated as being 16.

The facts that the acid value of the product was remarkably low as compared with that of the M-Acid, and that any absorption assigned to the carboxylic group was not confirmed from the infrared absorption spectrum have rendered it possible to confirm that the carboxylic-group of the M-Acid was modified with the CHDVE. Moreover, it can be seen from the increased molecular weight that polymerization reaction took place. That is to say, the objective phosphorus-containing carboxylic acid derivative has the structure represented by the following formula (n):

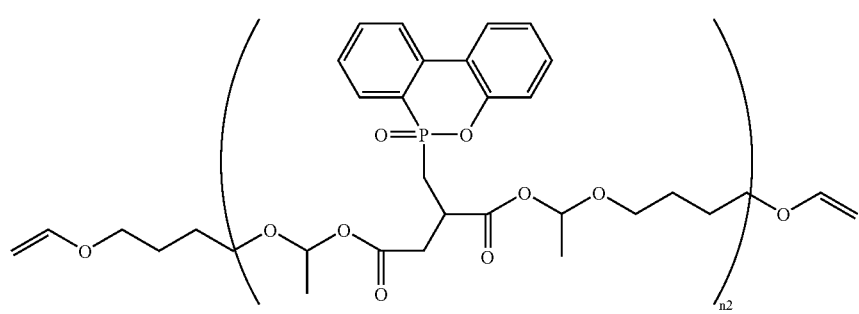

(n)

The objective phosphorus-containing carboxylic acid derivative had in its one molecule, 16 functional groups on an average represented by the foregoing formula (3) and had phosphorus atom content of 6.3% by weight.

In the following, the phosphorus-containing carboxylic acid derivative thus obtained is referred to as Block acid F. In the same manner as in Example 1, the solubility test and the storage stability test were carried out for the Block acid F. The results are shown in Table 1.

EXAMPLE 7

Phosphorus-Containing Carboxylic Acid Derivative Produced by Modifying M-Acid with Triethylene Glycol Divinyl Ether A four-neck flask equipped with a reflux condenser, a stirrer and a thermometer was charged with 30.9 parts by weight of M-acid which had been obtained in the foregoing Reference Example 3, 19.1 parts by weight of triethylene glycol divinyl ether (TEGDVE) and 50 parts by weight of methoxypropyl acetate (PMAc). The resultant mixture was stirred under the conditions of 100° C. for 3 hours. The reactivity which was calculated from the measured acid value was 99.1%. Then unreacted TEGDVE and unreacted PMAc were removed with the use of an evaporator under the conditions of 20 mmHg and 50° C.

Figure 10:
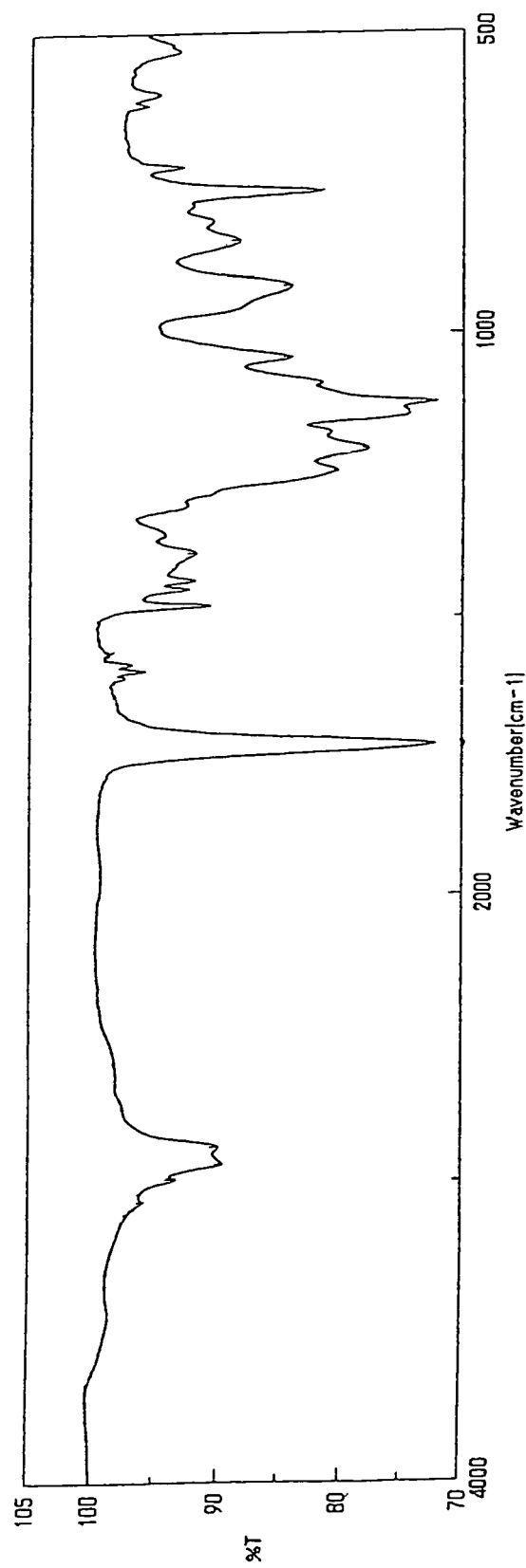
FIG. 10 is an infrared absorption spectrum of the product obtained in Example 7.
Figure 11:
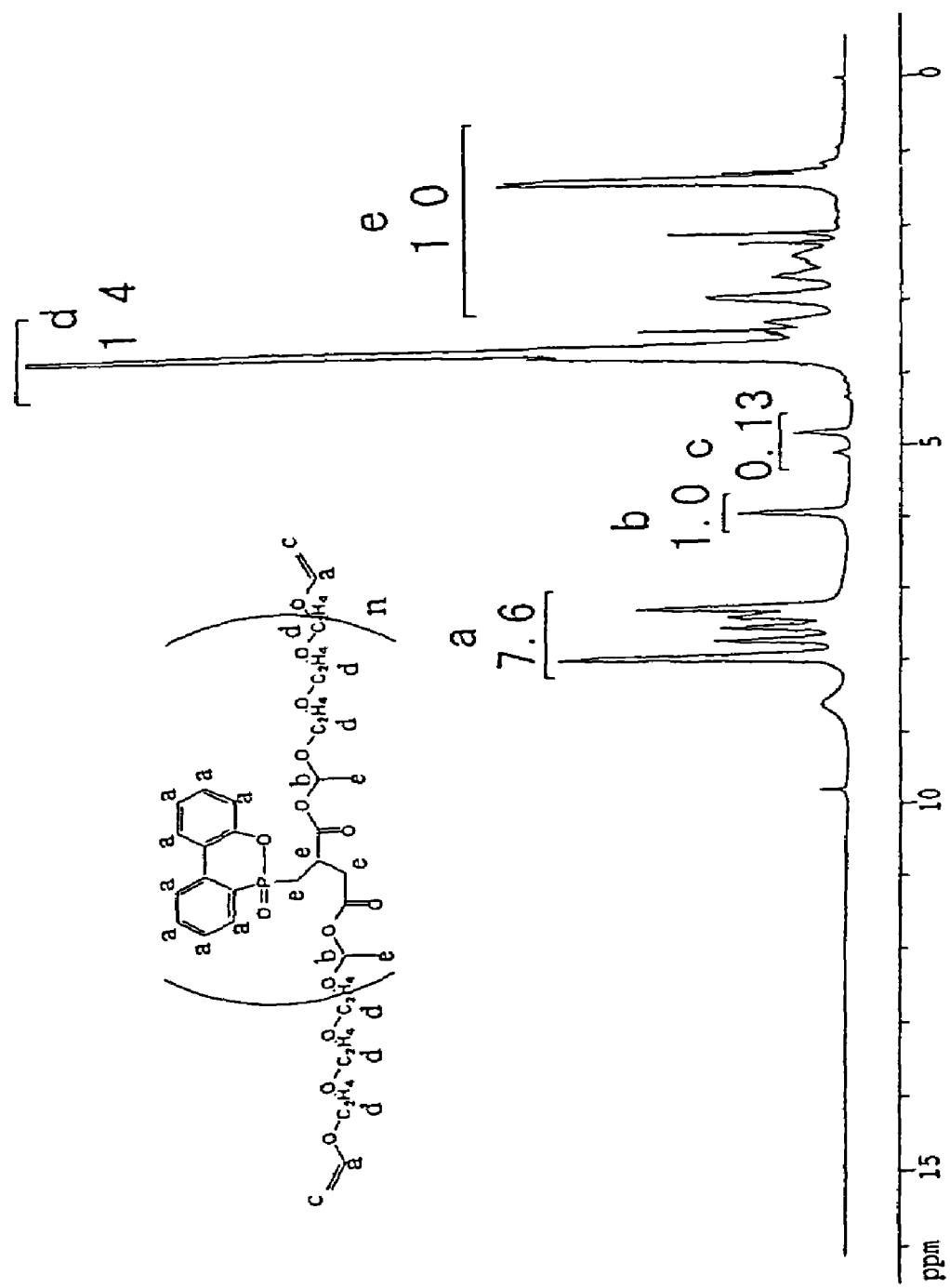
FIG. 11 is a nuclear magnetic resonance spectrum of the product obtained in Example 7.

The product thus obtained was light yellow transparent highly viscous liquid. The infrared absorption spectrum thereof is shown as FIG. 10, and the $^1$H-NMR spectrum thereof is shown as FIG. 11. Further the molecular weight thereof was measured in accordance with the foregoing GPC procedure. As a result, the weight-average molecular weight (Mw) was about 11,000, from which the average degree of polymerization "n" was calculated as being 20.

The facts that the acid value of the product was remarkably low as compared with that of the M-Acid, and that any absorption assigned to the carboxylic group was not confirmed from the infrared absorption spectrum have rendered it possible to confirm that the carboxylic group of the M-Acid was modified with the TEGDVE. Moreover, it can be seen from the increased molecular weight that polymerization reaction took place. That is to say, the objective phosphorus-containing carboxylic acid derivative has the structure represented by the following formula (o):

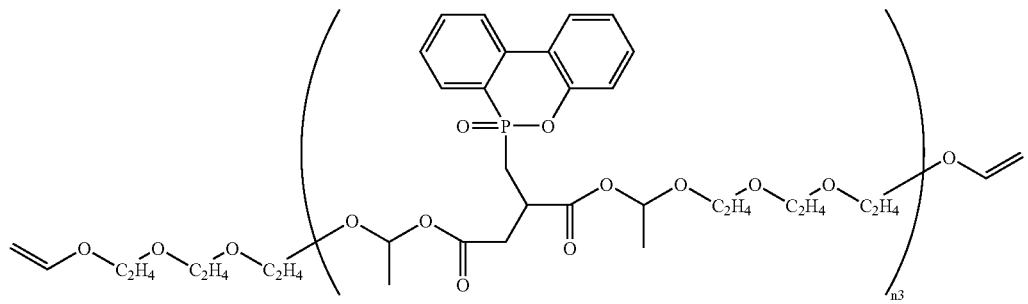

(o)

The objective phosphorus-containing carboxylic acid derivative had in its one molecule, 20 functional groups on an average represented by the foregoing formula (3) and had phosphorus atom content of 5.5% by weight.

In the following, the phosphorus-containing carboxylic acid derivative thus obtained is referred to as Block acid G.

In the same manner as in Example 1, the solubility test and the storage stability test carried out for the Block acid G. The results are shown in Table 1.

EXAMPLE 8

Phosphorus-Containing Carboxylic Acid Derivative Produced by Modifying PBTC with N-Propylvinyl Ether A four-neck flask equipped with a reflux condenser, a stirrer and a thermometer was charged with 46.6 parts by weight of PBTC and 53.4 parts by weight of n-propylvinyl ether. The resultant mixture was stirred under the conditions of 53° C. for 4 hours. The reactivity which was calculated from the measured acid value was 97.3%. Then unreacted n-propylvinyl ether was removed with the use of an evaporator under the conditions of 20 mmHg and 50° C. (the acid value after the vacuum concentration being 226 mg KOH/g).

Figure 12:
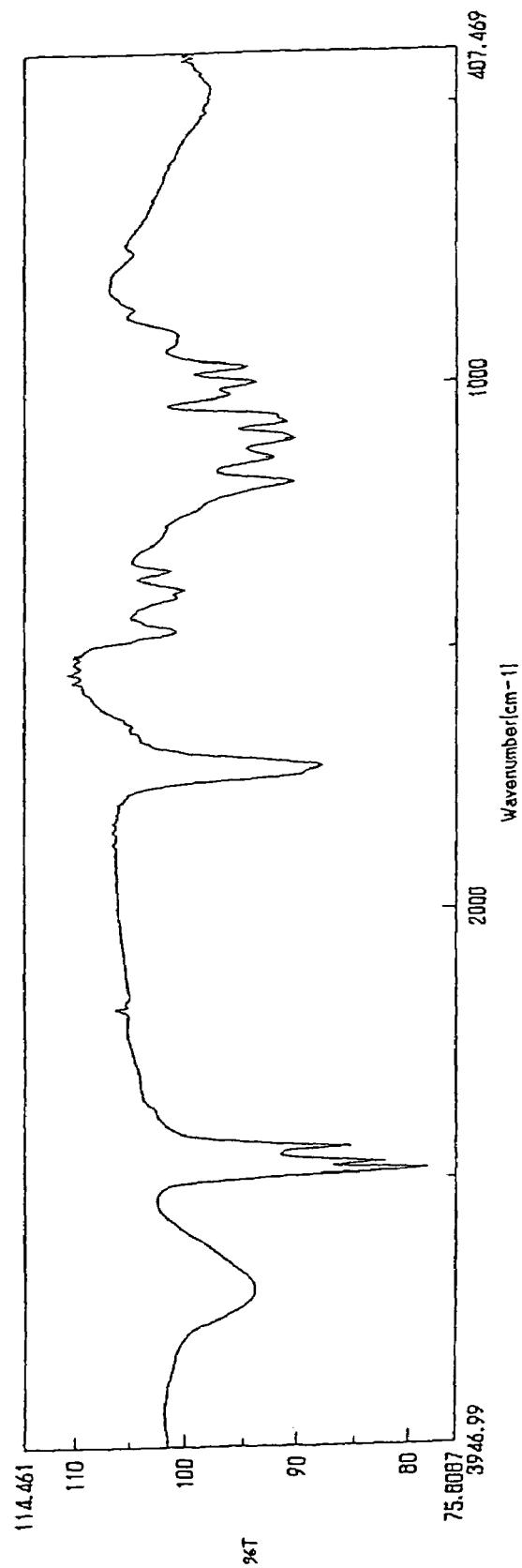
FIG. 12 is an infrared absorption spectrum of the product obtained in Example 8.

The product thus obtained was yellow transparent highly viscous liquid. The infrared absorption spectrum thereof is shown as FIG. 12.

The facts that the acid value of the product was remarkably low as compared with that of the PBTC before the reaction, and that any absorption assigned to the carboxylic group was not confirmed from the infrared absorption spectrum have rendered it possible to confirm that the carboxylic group of the PBTC was modified with the n-propylvinyl ether. That is to say, the objective phosphorus-containing carboxylic acid derivative has the structure represented by the following formula (p):

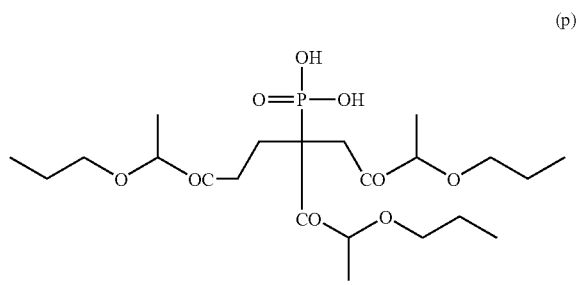

(p)

The objective phosphorus-containing carboxylic acid derivative had in its one molecule, 3 functional groups represented by the foregoing formula (2) and had phosphorus atom content of 6.45% by weight.

In the following, the phosphorus-containing carboxylic acid derivative thus obtained is referred to as Block acid H. In the same manner as in Example 1, the solubility test and the storage stability test were carried out for the Block acid H. The results are shown in Table 1.

EXAMPLE 9

Phosphorus-Containing Carboxylic Acid Derivative Produced by Modifying DEHP-ItaA with N-Propylvinyl Ether A four-neck flask equipped with a reflux condenser, a stirrer and a thermometer was charged with 56.5 parts by weight of DEHP-ItaA which had been obtained in the Reference Example 5, and 43.5 parts by weight of n-propylvinyl ether. The resultant mixture was stirred under the conditions of 10° C. for 6 hours. The reactivity which was calculated from the measured acid value was 97.2%. Then unreacted n-propylvinyl ether was removed with the use of an evaporator under the conditions of 20 mmHg and 50° C. (the acid value after the vacuum concentration being 11.8 mg KOH/g).

Figure 13:
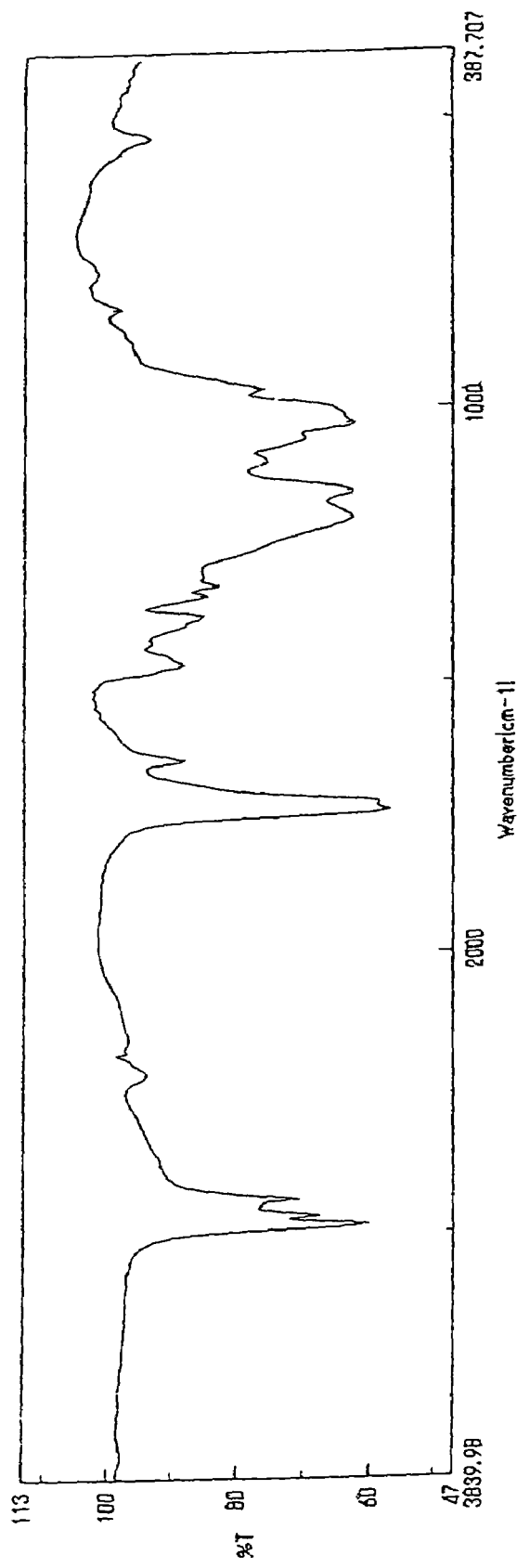
FIG. 13 is an infrared absorption spectrum of the product obtained in Example 9.

The product thus obtained was brown transparent highly viscous liquid. The infrared absorption spectrum thereof is shown as FIG. 13.

The facts that the acid value of the product was remarkably low as compared with that of the DEHP-ItaA before the reaction, and that any absorption assigned to the carboxylic group was not confirmed from the infrared absorption spectrum have rendered it possible to confirm that the carboxylic group of the DEHP-ItaA was modified with the n-propylvinyl ether. That is to say, the objective phosphorus-containing carboxylic acid derivative has the structure represented by the following formula (q):

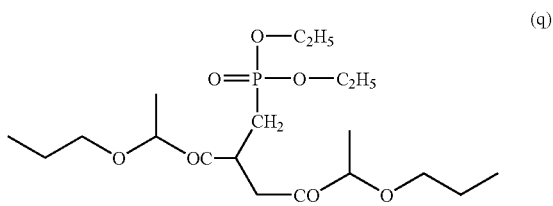

(q)

The objective phosphorus-containing carboxylic acid derivative had in its one molecule, 2 functional groups represented by the foregoing formula (2) and had phosphorus atom content of 7.59% by weight. In the following, the phosphorus-containing carboxylic acid derivative thus obtained is referred to as Block acid I. In the same manner as in Example 1, the solubility test and the storage stability test were carried out for the Block acid I. The results are shown in Table 1.

EXAMPLE 10

Phosphorus-Containing Carboxylic Acid Derivative Produced by Modifying DPHP-ItaA with N-Propylvinyl Ether A four-neck flask equipped with a reflux condenser, a stirrer and a thermometer was charged with 63.8 parts by weight of DPHP-ItaA which had been obtained in the Reference Example 7, and 36.2 parts by weight of n-propylvinyl ether. The resultant mixture was stirred under the conditions of 10° C. for 6 hours. The reactivity which was calculated from the measured acid value was 98.7%. Then unreacted n-propylvinyl ether was removed with the use of an evaporator under the conditions of 20 mmHg and 50° C. (the acid value after the vacuum concentration being 9.75 mg KOH/g).

The facts that the acid value of the product was remarkably low as compared with that of the DPHP-ItaA before the reaction, and that any absorption assigned to the carboxylic group was not confirmed from the infrared absorption spectrum have rendered it possible to confirm that the carboxylic group of the DPHP-ItaA was modified with the n-propylvinyl ether. That is to say, the objective phosphorus-containing carboxylic acid derivative has the structure represented by the following formula (r):

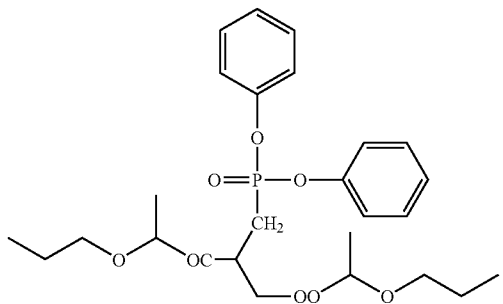

(r)

The objective phosphorus-containing carboxylic acid derivative had in its one molecule, 2 functional groups represented by the foregoing formula (2) and had phosphorus atom content of 6.14% by weight.

In the following, the phosphorus-containing carboxylic acid derivative thus obtained is referred to as Block acid J.

In the same manner as in Example 1, the solubility test and the storage stability test were carried out for the Block acid J. The results are shown in Table 1. For the purpose of comparison, the M-Acid that had been obtained in the Reference Example 3 was tested in the same manner as the above description.

Ep828 is epoxy resin of bisphenol type A (available from Japan Epoxy Resin Co., Ltd. under the trade name "Epicote 828").

EXAMPLE 11

Preparation of Film Blended with Block Acid A

A resin composition was prepared by mixing and agitating in a vial, 5.54 parts by weight of the Block acid A which had been synthesized in Example 1, 4.22 parts by weight of "YDPN 638" (trade name, available from Touto Kasei Co., Ltd.; epoxy resin of phenol novolak type) and 0.21 part by weight of "Nofcure-LC-1" (trade name, available from NOF Corporation; heat latent type catalyst).

Thereafter, the resin composition thus prepared was applied over a tin panel {JIS G3303 (SPTE), available from Japan Test Panel Osaka Co., Ltd.} with the use of a bar coater, followed by curing under the conditions of 200° C. for one hour to obtain a cured film of the resin composition. Then the resultant cured film was peeled apart from the tin panel to obtain a film A.

The film A was subjected to external appearance observation, solvent resistance test, combustibility test, coloring observation and heat resistance test. The results are shown in Table 2.

TABLE 1

| | | Solubility Test | | | | | | Stability |
|---|---|---|---|---|---|---|---|---|
| | | Acetone | MIBK | AcN | PMAc | Toluene | Ep 828 | Test |
| Example. 1 | Block Acid A | AA | AA | AA | AA | AA | AA | AA |
| Example. 2 | Block Acid B | AA | AA | AA | AA | AA | AA | AA |
| Example. 3 | Block Acid C | AA | AA | AA | AA | AA | AA | AA |
| Example. 4 | Block Acid D | AA | AA | AA | AA | AA | AA | AA |
| Example. 5 | Block Acid E | AA | AA | AA | AA | BB | AA | AA |
| Example. 6 | Block Acid F | AA | AA | AA | AA | BB | AA | AA |
| Example. 7 | Block Acid G | AA | AA | AA | AA | BB | AA | AA |
| Example. 8 | Block Acid H | AA | AA | AA | AA | BB | AA | AA |
| Example. 9 | Block Acid I | AA | AA | AA | AA | AA | AA | AA |
| Example. 10 | Block Acid J | AA | AA | AA | AA | AA | AA | AA |
| Ref. Example. 3 | M-Acid | BB | CC | CC | CC | CC | CC | Gellation |
| Marketed Product | PBTC | AA | AA | AA | AA | CC | CC | Hardened (15) |
| Ref. Example. 5 | DEHP-ItaA | AA | AA | AA | AA | CC | CC | Hardened (5) |
| Ref. Example. 7 | DEHP-ItaA | AA | AA | AA | AA | CC | CC | Hardened (5) |

{Remarks}

Regarding evaluation on the results of the solubility test, the marks mean as the following:

"AA" means compatible or completely soluble;

"BB" means that a certain turbidity was observed in the solution; and

"CC" means apparently not homogeneous.

Regarding evaluation on the results of the stability test, the marks mean as the following:

"AA" means no change observed on viscosity;

"Gellation" means that the sample rendered clear viscosity increase in the fluid; and "Hardened" means that a hardened product non-flowable in a vial even when the vial was brought down, and the figure in parentheses shows pasture of time before hardening expressed by minutes.

MIBK is an abbreviation of methyl isobutyl ketone.

AcN is an abbreviation of acetonitrile.

PMAc is an abbreviation of methoxypropyl acetate.

EXAMPLE 12

Preparation of Film Blended with Block Acid B

A resin composition was prepared by mixing and agitating in a vial, 5.76 parts by weight of the Block acid B which had been synthesized in Example 2, 4.06 parts by weight of YDPN 638 and 0.21 part by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film B.

In the same manner as the film A, the film B was subjected to external appearance observation, solvent resistance test, combustibility test, coloring observation and heat resistance test. The results are shown in Table 2.

EXAMPLE 13

Preparation of Film Blended with Block Acid C

A resin composition was prepared by mixing and agitating in a vial, 6.16 parts by weight of the Block acid C which had been synthesized in Example 3, 3.60 parts by weight of YDPN 638 and 0.21 part by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film C.

In the same manner as the film A, the film C was subjected to external appearance observation, solvent resistance test, combustibility test, coloring observation and heat resistance test. The results are shown in Table 2.

EXAMPLE 14

Preparation of Film Blended with Block Acid D

A resin composition was prepared by mixing and agitating in a vial, 5.61 parts by weight of the Block acid D which had been synthesized in Example 4, 4.09 parts by weight of YDPN 638 and 0.21 part by weight of Nofcure-LC-1.

Thereafter, the resin composition thus prepared was applied over the tin panel with the use of a bar coater, followed by curing under the conditions of 200° C. for one hour to obtain a cured film of the resin composition. Then the resultant cured film was peeled apart from the tin panel to obtain a film D.

In the same manner as the film A, the film D was subjected to external appearance observation, solvent resistance test, combustibility test, coloring observation and heat resistance test. The results are shown in Table 2.

EXAMPLE 15

Preparation of Film Blended with Block Acid A~2

A resin composition was prepared by mixing and agitating in a vial, 4.57 parts by weight of the Block acid A which had been synthesized in Example 1, 4.45 parts by weight of "Epicote 828" (trade name, available from Japan Epoxy Resin Co., Ltd.; epoxy resin of bisphenol type A), 0.74 part by weight of a derivative from CIC acid {tris(2-carboxyethyl)isocyanic acid} by n-propylvinyl ether and 0.21 part by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film A2.

In the same manner as the film A, the film A2 was subjected to external appearance observation, solvent resistance test, combustibility test, coloring observation and heat resistance test. The results are shown in Table 2.

EXAMPLE 16

Preparation of Film Blended with Block Acid A~3

A resin composition was prepared by mixing and agitating in a vial, 3.88 parts by weight of the Block acid A which had been synthesized in Example 1, 4.51 parts by weight of Epicote 828, 1.36 part by weight of a derivative from CIC acid by n-propylvinyl ether and 0.21 part by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film A3.

In the same manner as the film A, the film A3 was subjected to external appearance observation, solvent resistance test, combustibility test, coloring observation and heat resistance test. The results are shown in Table 2.

EXAMPLE 17

Preparation of Film Blended with Block Acid A~4

A resin composition was prepared by mixing and agitating in a vial, 2.51 parts by weight of the Block acid A which had been synthesized in Example 1, 4.65 parts by weight of Epicote 828, 2.61 part by weight of a derivative from CIC acid by n-propylvinyl ether and 0.21 part by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film A4.

In the same manner as the film A, the film A4 was subjected to external appearance observation, solvent resistance test, combustibility test, coloring observation and heat resistance test. The results are shown in Table 2.

EXAMPLE 18

Preparation of Film Blended with Block Acid A~5

A resin composition was prepared by mixing and agitating in a vial, 4.63 parts by weight of the Block acid A which had been synthesized in Example 1, 4.54 parts by weight of Epicote 828, 0.60 part by weight of a derivative from trimellitic acid by n-propylvinyl ether and 0.21 part by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film A5.

In the same manner as the film A, the film A5 was subjected to external appearance observation, solvent resistance test, combustibility test, coloring observation and heat resistance test. The results are shown in Table 2.

EXAMPLE 19

Preparation of Film Blended with Block Acid A~6

A resin composition was prepared by mixing and agitating in a vial, 3.93 parts by weight of the Block acid A which had been synthesized in Example 1, 4.69 parts by weight of Epicote 828, 1.14 part by weight of a derivative from trimellitic acid by n-propylvinyl ether and 0.21 part by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film A6.

In the same manner as the film A, the film A6 was subjected to external appearance observation, solvent resistance test, combustibility test, coloring observation and heat resistance test. The results are shown in Table 2.

COMPARATIVE EXAMPLE 1

Preparation of Film 1 not Blended with Block Acid A

A resin composition was prepared by mixing and agitating in a vial, 5.06 parts by weight of Epicote 828, 4.94 parts by weight of a derivative from CIC acid by n-propylvinyl ether and 0.21 part by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film 1.

In the same manner as the film A, the film 1 was subjected to external appearance observation, solvent resistance test, combustibility test, coloring observation and heat resistance test. The results are shown in Table 2.

COMPARATIVE EXAMPLE 2

Preparation of Film 2 Not Blended with Block Acid A

A resin composition was prepared by mixing and agitating in a vial, 5.69 parts by weight of Epicote 828, 4.32 part by weight of a derivative from trimellitic acid by n-propylvinyl ether and 0.21 parts by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film 2.

In the same manner as the film A, the film 2 was subjected to external appearance observation, solvent resistance test, combustibility test, coloring observation and heat resistance test. The results are shown in Table 2.

COMPARATIVE EXAMPLE 3

Preparation of Film M Blended with Unmodified M-Acid)

An attempt was made to prepare a resin composition by mixing and agitating in a vial, 5.06 parts by weight of Epicote 828, 4.94 parts by weight of a derivative from CIC acid by n-propylvinyl ether, 20.0 parts by weight of unmodified M-Acid and 0.21 parts by weight of Nofcure-LC-1. However, the M-Acid was not dissolved, thereby forming non-homogeneous and opaque suspension.

Thereafter, the resultant suspension was applied over the tin panel with the use of the bar coater, followed by curing under the conditions of 200° C. for one hour to obtain a cured film of the resin composition. Then the resultant cured film was peeled apart from the tin panel to obtain a film M which was non-uniform, opaque and extremely brittle.

In the same manner as the film A, the film M was subjected to external appearance observation, solvent resistance test, combustibility test, coloring observation and heat resistance test. The results are shown in Table 2.

EXAMPLE 20

Preparation of Film Blended with Block Acid E

A resin composition was prepared by mixing and agitating in a vial, 3.57 parts by weight of the Block acid E which had been synthesized in Example 5, 2.70 parts by weight of YDPN 638 and 0.13 parts by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film E.

In the same manner as the film A, the film E was subjected to external appearance observation, solvent resistance test, combustibility test, coloring observation and heat resistance test. The results are shown in Table 2.

EXAMPLE 21

Preparation of Film Blended with Block Acid F

A resin composition was prepared by mixing and agitating in a vial, 3.48 parts by weight of the Block acid F which had been synthesized in Example 6, 2.87 parts by weight of YDPN 638 and 0.13 part by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film F.

In the same manner as the film A, the film F was subjected to external appearance observation, solvent resistance test, combustibility test, coloring observation and heat resistance test. The results are shown in Table 2.

EXAMPLE 22

Preparation of Film Blended with Block Acid G

A resin composition was prepared by mixing and agitating in a vial, 3.61 parts by weight of the Block acid G which had been synthesized in Example 7, 2.62 parts by weight of YDPN 638 and 0.14 part by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film G.

In the same manner as the film A, the film G was subjected to external appearance observation, solvent resistance test, combustibility test, coloring observation and heat resistance test. The results are shown in Table 2.

EXAMPLE 23

Preparation of Film Blended with Block Acid H

A resin composition was prepared by mixing and agitating in a vial, 4.37 parts by weight of the Block acid H which had been synthesized in Example 8, 5.39 parts by weight of YDPN 638 and 0.21 part by weight of Nofcure-LC-1.

Thereafter, of the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film H.

In the same manner as the film A, the film H was subjected to external appearance observation, solvent resistance test, combustibility test, coloring observation and heat resistance test. The results are shown in Table 2.

EXAMPLE 24

Preparation of Film Blended with Block Acid I

A resin composition was prepared by mixing and agitating in a vial, 4.96 parts by weight of the Block acid I which had been synthesized in Example 9, 4.80 parts by weight of YDPN 638 and 0.21 part by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film I.

In the same manner as the film A, the film I was subjected to external appearance observation, solvent resistance test, combustibility test, coloring observation and heat resistance test. The results are shown in Table 2.

EXAMPLE 25

Preparation of Film Blended with Block Acid J

A resin composition was prepared by mixing and agitating in a vial, 5.48 parts by weight of the Block acid J which had been synthesized in Example 10, 4.29 parts by weight of YDPN 638 and 0.21 part by weight of Nofcure-LC-1.

Thereafter, the resin composition thus prepared was applied over the tin panel with the use of the bar coater, followed by curing under the conditions of 200° C. for one hour to obtain a cured film of the resin composition. Then the resultant cured film was peeled apart from the tin panel to obtain a film J.

In the same manner as the film A, the film J was subjected to external appearance observation, solvent resistance test, combustibility test, coloring observation and heat resistance test. The results are shown in Table 2.

TABLE 2

| | Film | P content (% by wt) | Film Appearance | Solvent Resistance | UL94TM | Coloring | Heat Resistance |
|---|---|---|---|---|---|---|---|
| Example 11 | A | 4.1 | AA | AA | V-0 | AA | AA |
| Example 12 | B | 3.5 | AA | AA | V-0 | AA | AA |
| Example 13 | C | 3 | AA | AA | V-0 | AA | AA |
| Example 14 | D | 2 | AA | AA | V-0 | AA | AA |
| Example 15 | A2 | 3.5 | AA | AA | V-0 | AA | AA |
| Example 16 | A3 | 3 | AA | AA | V-0 | AA | AA |
| Example 17 | A4 | 4.1 | AA | AA | V-0 | AA | AA |
| Example 18 | A5 | 4.1 | AA | AA | V-0 | AA | AA |
| Example 19 | A6 | 4.1 | AA | AA | V-0 | AA | AA |
| Example 20 | E | 4.1 | AA | AA | V-0 | AA | AA |
| Example 21 | F | 4.1 | AA | AA | V-0 | AA | AA |
| Example 22 | G | 4.1 | AA | AA | V-0 | AA | AA |
| Example 23 | H | 3.8 | Yellow & transparent | AA | V-0 | AA | AA |
| Example 24 | I | 4.9 | Yellow & transparent | AA | V-0 | AA | AA |
| Example 25 | J | 4.3 | Yellow & transparent | AA | V-0 | AA | AA |
| Comp. Example 1 | 1 | 0 | AA | AA | CC | CC | CC |
| Comp. Example 2 | 2 | 0 | AA | AA | CC | CC | CC |
| Comp. Example 3 | M | 1.5 | Not uniform | CC | CC | CC | BB |

{Remarks}

"P content (% by wt)" means Phosphorus component with the dimension of % by weight calculated from blending composition.

Regarding Film appearance, it was visually observed and "AA" means colorless and transparent Regarding the evaluation of Solvent resistance test, "AA" means free from defect and "CC" means that the film was apparently suffered from damages.

UL94TM indicates results of combustion test and "CC" means non-standardized.

Regarding the evaluation of the coloring observation, "AA" means without yellowing before and after heating and "CC" means with yellowing apparently confirmed before or after heating.

Regarding evaluation of the heat resistance test, "AA" means that the thermal decomposition temperature of the sample being 330° C. or higher, "BB" means that the thermal decomposition temperature of the sample being lower than 330° C. and at least 310° C., and "CC" means that the thermal decomposition temperature being lower than 310° C.

EXAMPLE 26

Preparation of Laminate A Using Block Acid A as Flame Retardant

A resin composition was prepared by mixing and agitating in a vial, 3.77 parts by weight of the Block acid A which had been synthesized in Example 1, 3.24 parts by weight of "YDCN 701" (trade name, available from Touto Kasei Co., Ltd.; epoxy resin of cresol novolak type), 0.35 parts by weight of "Nofcure-LC-1" (trade name, available from NOF Corporation; heat latent type catalyst), and 3.90 parts by weight of methyl ethyl ketone.

Thereafter, the resin composition thus prepared was applied over M surface of a copper foil "3EC-111" (trade name, available from Mitsui Mining and Smelting Co., Ltd. and having the thickness of 18 μm) with the use of the bar coater. After prebaking at 145° C. for 3 minutes, a tack-free resin coated surface was obtained. Subsequently, three sheets of the resultant resin coated foils were laminated so that the copper foil and the resin coating were alternately superimposed, and the exposed resin coated surface was covered with S surface of the copper foil, followed by curing with a press under pressing conditions of 180° C., 60 minutes and 200 kgf/cm². After the pressing, there was obtained a laminate in the form of plate having a film thickness of about 200 μm.

EXAMPLE 27

Preparation of LED Covered with Resin Composition Blended with Block Acid A

A resin composition was prepared by mixing and agitating in a vial, 4.70 parts by weight of the Block acid A which had been synthesized in Example 1, 3.24 parts by weight of "EHPE-3150" (trade name, available from Daicel Chemical Industries Ltd.; alicyclic epoxy resin in solid form), 0.40 part by weight of "Nofcure-LC-1" (trade name, available from NOF Corporation; a heat latent type catalyst) and 5,40 parts by weight of methyl ethyl ketone.

Thereafter, an LED (light emitting diode, available on the market under the trade name "NSPW310BS") was dipped in the resin composition thus prepared, then dried at room temperature for 10 minutes, and heated at 100° C. for one hour further at 120° C. for one hour. The covering film thus obtained was colorless transparent, and had a film thickness of about 30 μm.

The covered LED was subjected to inflammation test by exposing the same in the blue flame of methane gas burner. A non-covered LED caught fire after about 4 seconds from the start of the test, and completely burnt even when it was kept away from the flame. On the contrary, the covered LED did not catch fire for about 25 seconds thereafter, and when it was kept at a distance after catching fire, the flame caught thereby was self-extinguished.

INDUSTRIAL APPLICABILITY

The phosphorus-containing carboxylic acid derivative according to the present invention is utilized as a flame retardant, coloring preventive agent and heat resistance-imparting agent, and for a resin molded article, laminate, resin casting material, resin sealing material, adhesive, covering material and the like on the basis of such characteristics that are imparted thereto as self and heat resistance-imparting agent, and for a resin molded article, laminate, resin casting material, resin sealing material, adhesive, covering material and the like on the basis of such characteristics that are imparted thereto as self fire-extinguishing property, flame retardancy, coloring preventiveness and heat resistance.

The invention claimed is:

1. A phosphorus-containing carboxylic acid derivative which has a group containing phosphorus atom and has in its molecule, a group represented by the following formula (2):

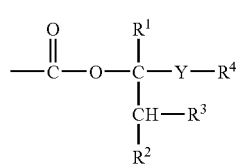

wherein $R^1$, $R^2$ and $R^3$ are each hydrogen atom or a hydrocarbon group having 1 to 18 carbon atoms, $R^4$ is a hydrocarbon group having 1 to 18 carbon atoms, $R^3$ and $R^4$ may be bonded to each other, and Y is oxygen atom or sulfur atom.

2. A phosphorus-containing carboxylic acid derivative which has a group containing phosphorus atom and has in its molecule, a group represented by the following formula (3):

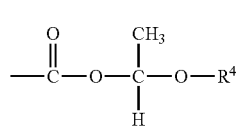

wherein $R^4$ is a hydrocarbon group having 1 to 18 carbon atoms.

3. A phosphorus-containing carboxylic acid derivative which is a polyhemiacetal phosphorus-containing carboxylic acid derivative and comprises, as a repeating unit, a group represented by the following formula (4):

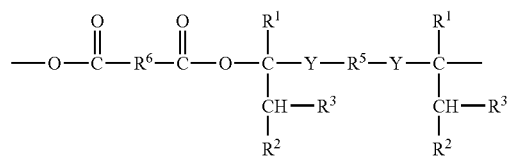

wherein $R^1$, $R^2$ and $R^3$ are each hydrogen atom or a hydrocarbon group having 1 to 18 carbon atoms, Y is oxygen atom or sulfur atom, $R^5$ is a bivalent organic group having 1 to 25 carbon atoms, and $R^6$ is a bivalent organic group which has 1 to 30 carbon atoms and comprises a group containing phosphorus atoms.

4. A phosphorus-containing carboxylic acid derivative which is a polyhemiacetal phosphorus-containing carboxylic acid derivative and comprises, as a repeating unit, a group represented by the following formula (5):

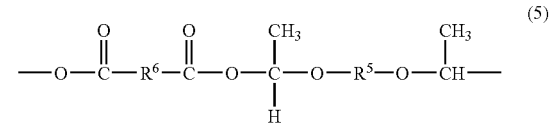

wherein $R^5$ is a bivalent organic group having 1 to 25 carbon atoms, and $R^6$ is a bivalent organic group which has 1 to 30 carbon atoms and comprises a group containing phosphorus atom.

5. The phosphorus-containing carboxylic acid derivative according to claim 1, wherein said group containing phosphorus atom is represented by the following formula (7)

wherein $R^7$ is hydrogen atom or an organic group having 1 to 20 carbon atoms, $R^8$ is an organic group having 1 to 20 carbon atoms, and when both $R^7$ and $R^8$ are an organic group, they may be bonded to each other.

6. The phosphorus-containing carboxylic acid derivative according to claim 1, wherein said group containing phosphorus atom is represented by the following formula (8):

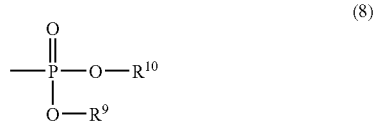

wherein $R^9$ and $R^{10}$ are each hydrogen atom or an organic group having 1 to 20 carbon atoms, and when both $R^9$ and $R^{10}$ are an organic group, they may be bonded to each other.

7. The phosphorus-containing carboxylic acid derivative according to claim 1, wherein said group containing phosphorus atom is represented by the following formula (10):

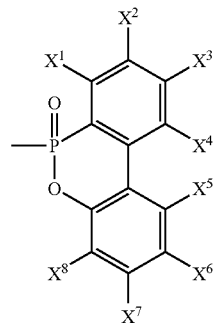

wherein $X^1$ to $X^8$, which are each an atom or a group that may be the same as or different from one another, are each hydrogen atom, a halogen atom or a hydrocarbon group having 1 to 5 carbon atoms.

8. A flame retardant comprising as an ingredient, the phosphorus-containing carboxylic acid derivative as set forth in claim 1.

9. A process for producing a phosphorus-containing carboxylic acid derivative as set forth in claim 1, which comprises a step of reacting a phosphorus-containing carboxylic acid compound bearing both a carboxylic group and phosphorus atom with a vinyl ether compound, a vinyl thioether compound, a divinyl ether compound or a divinyl thioether compound.

10. The process for producing a phosphorus-containing carboxylic acid derivative according to claim 9, wherein said phosphorus-containing carboxylic acid compound is produced by subjecting (A) a P—H group-containing phosphorus compound and (B) an unsaturated carboxylic acid each as a starting raw material to Michael addition reaction by (i) using acetonitrile or methoxypropyl acetate as a principal reaction solvent at (ii) a reaction temperature in the range of 50 to 150° C.

11. A resin composition which comprises (a) a synthetic resin bearing in its molecule, at least two reactive groups that are each reactive with a carboxylic group and (b) the phosphorus-containing carboxylic acid derivative as set forth in claim 1.

12. The resin composition according to claim 11, wherein said reactive groups are each an epoxy group.

13. A resin-molded article obtained by curing the resin composition as set forth in claim 11.

14. A laminated sheet comprising a substrate and the resin-molded article as set forth in claim 13.

15. A covered article comprising a substrate and a covering layer formed by applying said resin composition as set forth in claim 11 over at least a part of surfaces of said substrate.

16. The covered article according to claim 15, wherein said covering layer is further cured.

17. The phosphorus-containing carboxylic acid derivative according to claim 3, wherein said group containing phosphorus atom is represented by the following formula (7)

wherein $R^7$ is hydrogen atom or an organic group having 1 to 20 carbon atoms, $R^8$ is an organic group having 1 to 20 carbon atoms, and when both $R^7$ and $R^8$ are an organic group, they may be bonded to each other.

18. The phosphorus-containing carboxylic acid derivative according to claim 3, wherein said group containing phosphorus atom is represented by the following formula (8):

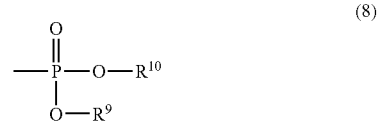

wherein $R^9$ and $R^{10}$ are each hydrogen atom or an organic group having 1 to 20 carbon atoms, and when both $R^9$ and $R^{10}$ are an organic group, they may be bonded to each other.

19. The phosphorus-containing carboxylic acid derivative according to claim 3, wherein said group containing phosphorus atom is represented by the following formula (10):

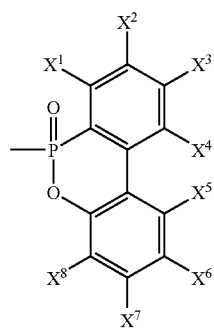

(10)

wherein $X^1$ to $X^8$, which are each an atom or a group that may be the same as or different from one another, are each hydrogen atom, a halogen atom or a hydrocarbon group having 1 to 5 carbon atoms.

20. A flame retardant comprising as an ingredient, the phosphorus-containing carboxylic acid derivative as set forth in claim 6.

21. A flame retardant comprising as an ingredient, the phosphorus-containing carboxylic acid derivative as set forth in claim 5.

22. A flame retardant comprising as an ingredient, the phosphorus-containing carboxylic acid derivative as set forth in claim 3.

23. A flame retardant comprising as an ingredient, the phosphorus-containing carboxylic acid derivative as set forth in claim 2.

24. A process for producing a phosphorus-containing carboxylic acid derivative as set forth in claim 3, which comprises a step of reacting a phosphorus-containing carboxylic acid compound bearing both a carboxylic group and phosphorus atom with a vinyl ether compound, a vinyl thioether compound, a divinyl ether compound or a divinyl thioether compound.

25. A resin composition which comprises (a) a synthetic resin bearing in its molecule, at least two reactive groups that are each reactive with a carboxylic group and (b) the phosphorus-containing carboxylic acid derivative as set forth in claim 3.

26. The phosphorus-containing carboxylic acid derivative according to claim 2, wherein said group containing phosphorus atom is represented by the following formula (7):

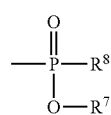

(7)

wherein $R^7$ is hydrogen atom or an organic group having 1 to 20 carbon atoms, $R^8$ is an organic group having 1 to 20 carbon atoms, and when both $R^7$ and $R^8$ are an organic group, they may be bonded to each other.

27. The phosphorus-containing carboxylic acid derivative according to claim 2, wherein said group containing phosphorus atom is represented by the following formula (8):

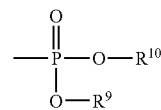

(8)

wherein $R^9$ and $R^{10}$ are each hydrogen atom or an organic group having 1 to 20 carbon atoms, and when both $R^9$ and $R^{10}$ are an organic group, they may be bonded to each other.

28. The phosphorus-containing carboxylic acid derivative according to claim 2, wherein said group containing phosphorus atom is represented by the following formula (10):

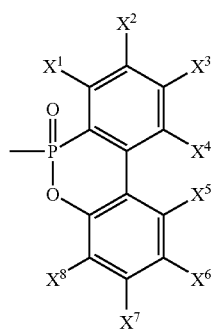

(10)

wherein $X^1$ to $X^8$, which are each an atom or a group that may be the same as or different from one another, are each hydrogen atom, a halogen atom or a hydrocarbon group having 1 to 5 carbon atoms.

29. A flame retardant comprising as an ingredient, the phosphorus-containing carboxylic acid derivative as set forth in claim 2.

30. A process for producing a phosphorus-containing carboxylic acid derivative as set forth in claim 2, which comprises a step of reacting a phosphorus-containing carboxylic acid compound bearing both a carboxylic group and phosphorus atom with a vinyl ether compound, a vinyl thioether compound, a divinyl ether compound or a divinyl thioether compound.

31. A resin composition which comprises (a) a synthetic resin bearing in its molecule, at least two reactive groups that are each reactive with a carboxylic group and (b) the phosphorus-containing carboxylic acid derivative as set forth in claim 2.

32. A resin-molded article obtained by curing the resin composition as set forth in claim 31.

33. A laminated sheet comprising a substrate and the resin-molded article as set forth in claim 32.

34. A covered article comprising a substrate and a covering layer formed by applying said resin composition as set forth in claim 31 over at least a part of surfaces of said substrate.

35. A phosphorus-containing carboxylic acid derivative which has a group containing phosphorus atom and has in its molecule, a group represented by the following formula (1):

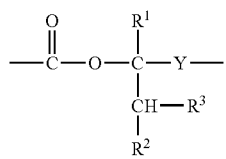

(1)

wherein $R^1$, $R^2$ and $R^3$ are each hydrogen atom or a hydrocarbon group having 1 to 18 carbon atoms, and Y is oxygen atom or sulfur atom, and wherein said group containing phosphorus atom is represented by the following formula (10):

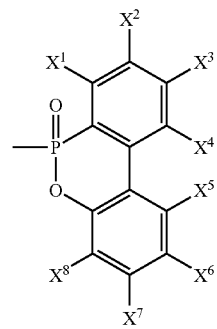

(10)

wherein $X^1$ to $X^8$, which are each an atom or a group that may be the same as or different from one another, are each hydrogen atom, a halogen atom or a hydrocarbon group having 1 to 5 carbon atoms.

* * * * *